(12) United States Patent
Maher et al.

(10) Patent No.: US 11,666,710 B2
(45) Date of Patent: Jun. 6, 2023

(54) DELIVERY DEVICES FOR THERAPEUTIC SUBSTANCES

(71) Applicant: BLUEROCK THERAPEUTICS LP, Cambridge, MA (US)

(72) Inventors: Matthew Gardner Maher, Toronto (CA); Angel Leonardo Guerrero Palacio, Toronto (CA); Philippe Marchand, Pointe-Claire (CA)

(73) Assignee: BLUEROCK THERAPEUTICS LP, Cambridge, MA (US)

( * ) Notice: Subject to any disclaimer, the term of this patent is extended or adjusted under 35 U.S.C. 154(b) by 0 days.

(21) Appl. No.: 17/229,218

(22) Filed: Apr. 13, 2021

(65) Prior Publication Data

US 2021/0316081 A1    Oct. 14, 2021

Related U.S. Application Data

(60) Provisional application No. 63/009,572, filed on Apr. 14, 2020.

(51) Int. Cl.
*A61M 5/32* (2006.01)
*A61M 5/315* (2006.01)

(52) U.S. Cl.
CPC ........ *A61M 5/3234* (2013.01); *A61M 5/3157* (2013.01)

(58) Field of Classification Search
CPC .............. A61M 5/3234; A61M 5/3157; A61M 5/3293; A61M 5/31586; A61M 5/34; A61M 25/0631; A61M 25/0606; A61K 35/12
See application file for complete search history.

(56) References Cited

U.S. PATENT DOCUMENTS

| | | | |
|---|---|---|---|
| 2005/0124007 A1* | 6/2005 | Sah | A61P 25/16 435/368 |
| 2006/0100577 A1* | 5/2006 | Shue | A61M 5/3234 604/110 |
| 2015/0133946 A1* | 5/2015 | Horvath | A61F 9/00781 606/108 |

FOREIGN PATENT DOCUMENTS

WO    2010/029054 A1    3/2010

OTHER PUBLICATIONS

International Search Report and Written Opinion dated Aug. 17, 2021 received in International Application No. PCT/US2021/026988.

* cited by examiner

*Primary Examiner* — Tasnim Mehjabin Ahmed
(74) *Attorney, Agent, or Firm* — Scully Scott Murphy and Presser

(57) ABSTRACT

In some embodiments, a delivery device includes a device actuator and a cannula portion through which a therapeutic substance is ejected. The cannula portion includes an outer shaft, a needle that is configured to move through the outer shaft, and a plunger that is configured to move through the needle, forming a positive displacement arrangement.

62 Claims, 17 Drawing Sheets

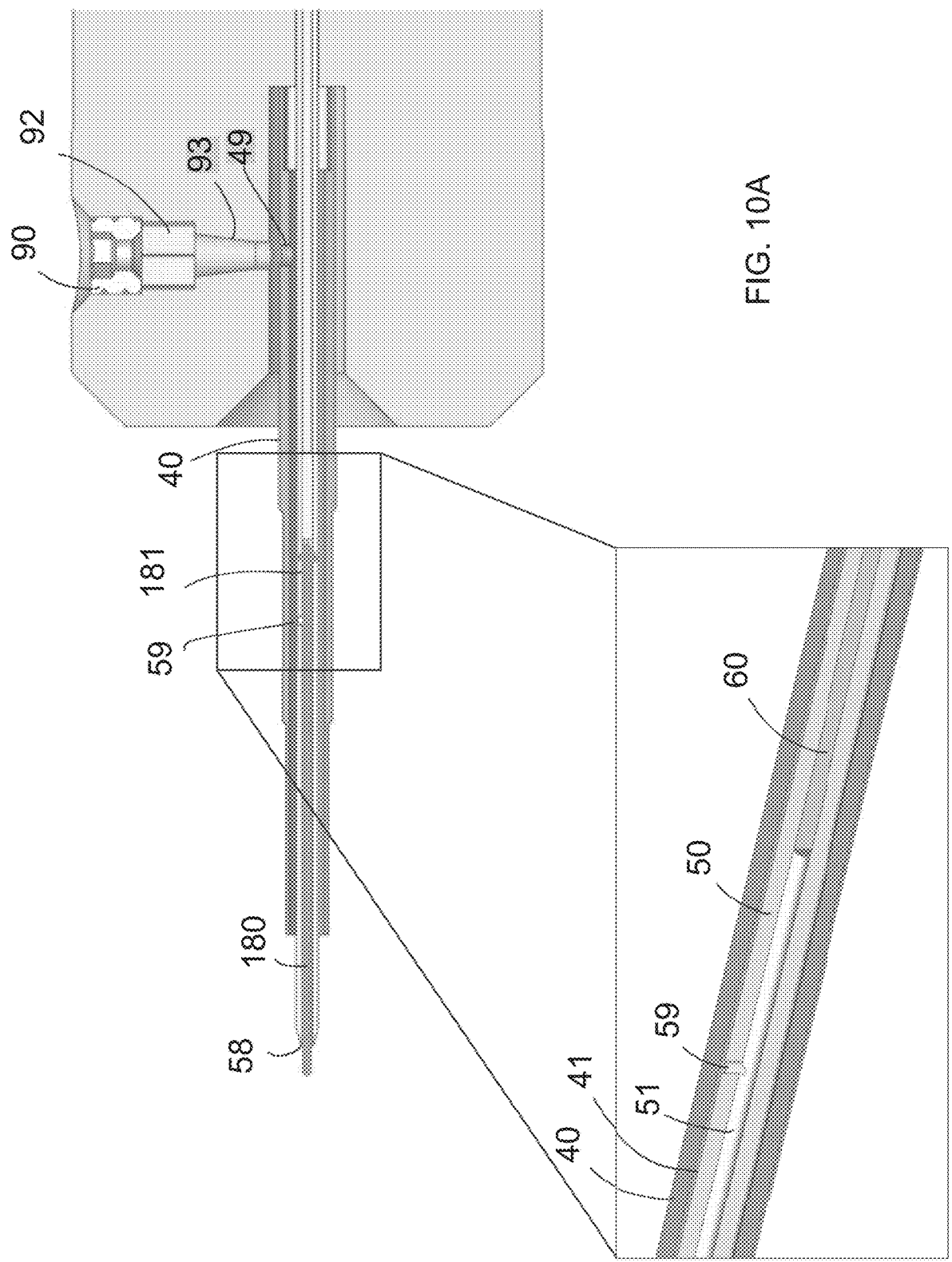

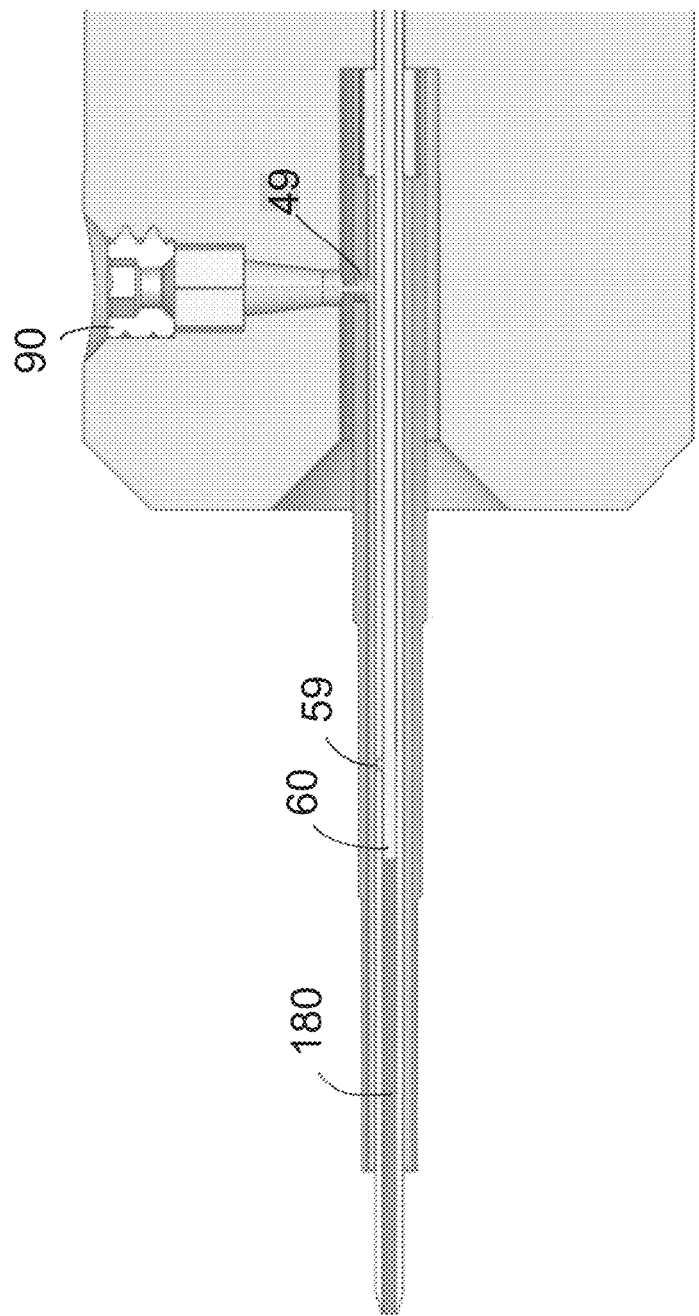

DELIVERY DEVICES FOR THERAPEUTIC SUBSTANCES

CROSS-REFERENCE TO RELATED APPLICATIONS

The subject application claims the benefit of provisional U.S. Patent Application No. 63/009,572, filed on Apr. 14, 2020. The entire disclosure of provisional U.S. Patent Application No. 63/009,572 is incorporated by reference herein.

FIELD

Disclosed embodiments are related to delivery devices and related methods of use.

BACKGROUND

Therapeutic substances are administered to patients through a variety of methods. Various routes of administration are possible, including: oral, inhalation, topical, intravascular, intramuscular, subcutaneous, intraperitoneal, rectal/vaginal, transluminal, and more tissue-specific routes (e.g., intrathecal, intraventricular, and intra-articular).

Cell-based therapeutics are commonly administered using conventional delivery devices, such as a needle and syringe, or a balloon-dilating catheter. Injection of cell-based therapeutics through skin or mucosa may help to bypass some of the body's defense barriers, and may enable delivery of cell-based therapeutics to a specific site.

SUMMARY

In some embodiments, a delivery device is provided. The delivery device may include a device actuator, a needle having a needle lumen, and a plunger configured to move through the needle lumen, is provided. Actuation of the device actuator may cause the needle to move through the shaft lumen in a retraction direction, and may cause the plunger to move through the needle lumen in a deployment direction, the retraction direction being opposite to the deployment direction.

In some embodiments, a delivery device is provided. The delivery device may include a device actuator, an outer shaft having a shaft lumen and a needle having a needle lumen, is provided. The needle may be configured to move through the outer shaft lumen. The delivery device may also include a plunger that is configured to move through the needle lumen. Actuation of the device actuator may cause the needle to move a first distance relative to the outer shaft, and may cause the plunger to move a second distance relative to the outer shaft, the first distance being different from the second distance.

In some embodiments, a delivery device is provided. The delivery device may include a device housing, a device actuator that is rotatably mounted relative to the device housing, a needle having a needle lumen, and a plunger that is configured to move through the needle lumen, is provided. Rotation of the device actuator may cause the plunger to move through the needle lumen.

In some embodiments, a method of delivering a substance through a delivery device is provided. The method may include rotating a device actuator at least 10 complete rotations, resulting in delivery of a volume of a substance through an outlet of the needle, wherein the volume is between 1 microliter to 50 microliters, inclusive.

In some embodiments, a method of loading cells into a delivery device is provided. The method may include moving cells into a needle lumen through a delivery end of a needle, venting air out of the needle lumen through a vent in the needle as the cells are moved into the needle lumen, and, after the cells are moved into the needle lumen, closing fluid communication through the vent.

In some embodiments, a delivery device is provided. The delivery device may include a device housing and a needle. The needle may include a delivery end, a shaft, and a needle lumen extending through the shaft. The delivery device may also include a plunger that is configured to move through the needle lumen. The needle may also include a vent in the shaft, the vent being spaced from the delivery end.

In some embodiments, a delivery device is provided. The delivery device may include a device actuator, an outer shaft having a shaft lumen, and a needle having a needle lumen. The needle lumen may have a diameter of between 0.1 mm to 0.7 mm, inclusive, and the needle may be configured to move through the shaft lumen. The delivery device may also include a plunger that is configured to move through the needle lumen, where the plunger has a travel distance relative to the outer shaft of at least 100 mm.

In some embodiments, a method of delivering cells through a delivery device is provided. The method may include moving a needle of a delivery device to a target site and occupying a volume of space at the target site with the needle. The method may also include actuating a device actuator, causing the needle to retract from the volume of space and a plunger to move through a needle lumen of the needle toward the volume of space, simultaneously delivering cells into the volume of space with cells as the needle retracts from the volume of space.

In some embodiments, a delivery device is provided. The delivery device may include a device actuator, a needle having a needle lumen, a plunger that is configured to move through the needle lumen, and an indicator having indicia indicating dosage delivered. The indicator may be mechanically coupled to the device actuator such that actuation of the device actuator causes the indicia of the indicator to physically move without input of electricity.

In some embodiments, a delivery device is provided. The delivery device may include a device housing and a needle having a needle lumen. The needle lumen may have a constant diameter throughout its length. The delivery device may also include a plunger that is configured to move through the needle lumen, and a therapeutic substance that is entirely contained within the needle lumen.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 10A is a cross-sectional view of a delivery device undergoing a loading process, according to one embodiment;

FIG. 10C is a cross-sectional view of the delivery device of FIG. 10B in a loaded and primed state;

DETAILED DESCRIPTION

Figure 1:
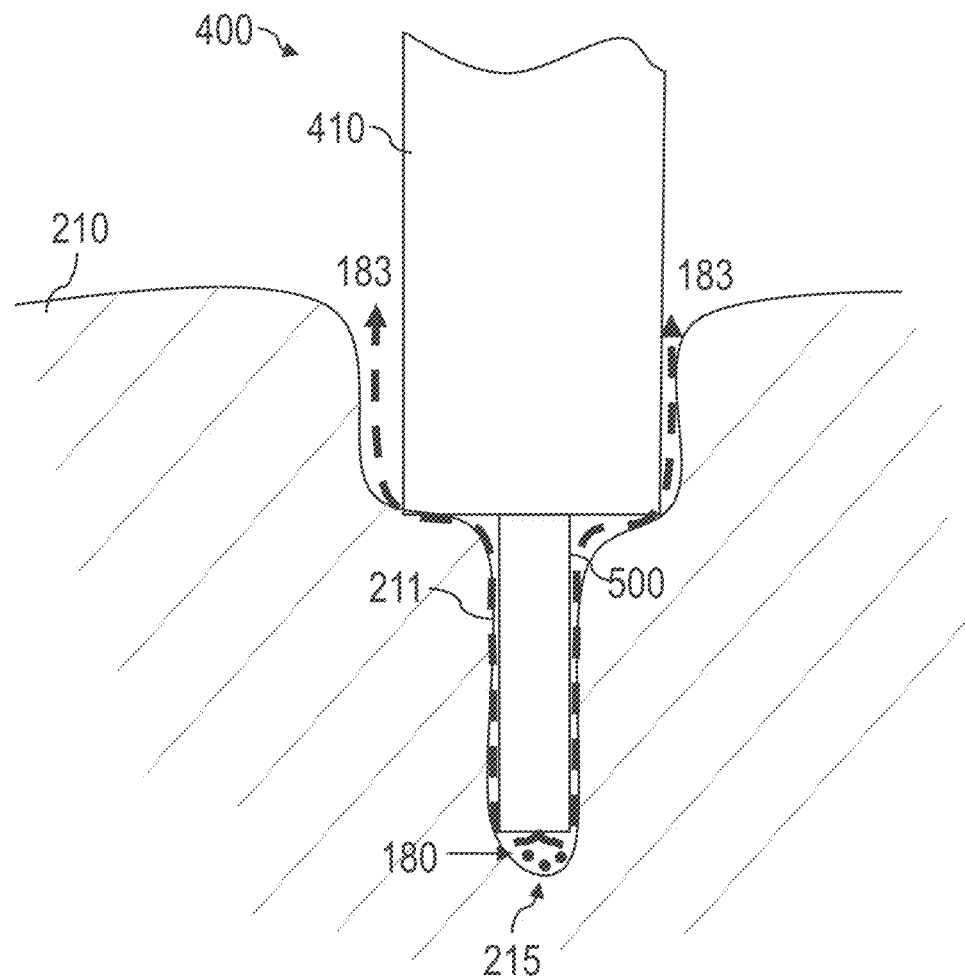
FIG. 1 is a schematic illustration of a delivery device creating backflow of a therapeutic substance during injection of the therapeutic substance.

With some conventional delivery devices, the delivery device is inserted into tissue to reach a target site, a therapeutic substance is ejected out of the delivery device and into the target site, and then the delivery device is withdrawn from the target site. As discussed in more detail below, the inventors have appreciated that some of these conventional delivery devices experience unwanted backflow of the therapeutic substance out of the target site as the therapeutic substance is injected into the target site. The inventors have also appreciated that, with some conventional cell delivery devices, the cells provided in a fluid solution held in the devices experience a "cell settling" effect in which cells may clump within the device, e.g. due to gravity. Cell settling may result in delivery of non-uniform concentrations of cells, which in turn may cause variations in cell seeding density. The inventors have also appreciated that some conventional delivery devices do not limit a user from rapidly ejecting a therapeutic substance. The inventors have recognized that fast ejection rates may have detrimental effects for the therapeutic substance. For example, with cell delivery, fast ejection rates may decrease cell viability, e.g. due to damage to cells through shear stresses. The inventors have also recognized that fast ejection rate may cause unnecessary tissue trauma. With some conventional delivery devices, therapeutic substances are back-loaded into the device. The inventors have also appreciated that back-loading may require the therapeutic substance to traverse a long pathway through the device before reaching the delivery end of the device. Due to the long travel distance, some of the therapeutic substance may remain trapped within the pathway of the delivery device instead of being delivered, resulting in wastage of the therapeutic substance. Furthermore, in some conventional devices, the pathway may include changes in diameter and/or may include non-smooth transitions, either of which may subject the therapeutic substance to detrimental effects.

The inventors have recognized the need for delivery devices that address some or all of the above-described problems of conventional delivery devices.

Some embodiments described herein include a delivery device that delivers a therapeutic substance via a positive displacement arrangement in which a plunger moves through a needle lumen to eject the therapeutic substance out of the needle. In some embodiments, the therapeutic substance to be delivered are cells, or other particles having a certain diameter. It should be appreciated, however, that the therapeutic substance is not limited to cells or particles. Wherever discussed hereinafter, "cells" may be substituted with any other therapeutic substance, as appropriate.

According to one aspect, the delivery device may be configured to reduce backflow of the therapeutic substance out of the target site during injection of the therapeutic substance into the target site. In some embodiments, the needle may be arranged to retract while the plunger advances. The needle may create a cavity in the tissue for the therapeutic substance. As the therapeutic substance is ejected from the needle, the needle is retracted, thereby providing a volume of space in the created cavity for the therapeutic substance to inhabit.

FIG. 1 illustrates this backflow concept via a delivery device 400 having an outer cannula 410 and a needle 500. The outer cannula 410 and the needle 500 of the delivery device have been inserted into tissue 210, and the needle 500 forms a cavity 211 in the tissue 210. A therapeutic substance 180 is being delivered to a target site 215. Because the target site 215 is occupied by the needle 500, the therapeutic substance 180 may be forced upwards 183 between the tissue cavity 211 and the delivery device 400 (instead of occupying the target site 215).

Figure 2:
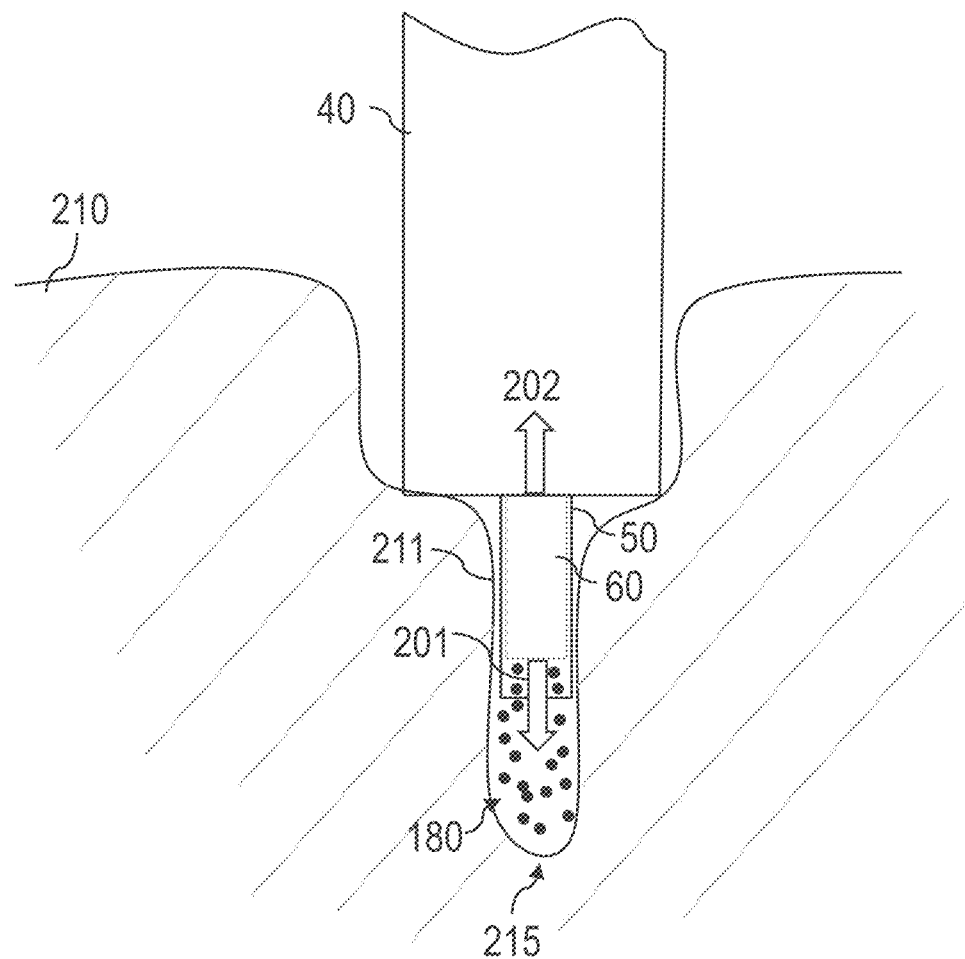
FIG. 2 is a schematic illustration of one embodiment of a delivery device according to aspects described herein, in which the potential backflow issue experienced by the FIG. 1 delivery device may be reduced.

In contrast, FIG. 2 is a schematic of one embodiment of a delivery device according to aspects described herein, in which the potential backflow issue described above may be reduced. The delivery device includes an outer shaft 40, a needle 50 that is moveable within the outer shaft 40, and a plunger 60 that is moveable within the needle 50. As the plunger 60 advances 201 in a distal direction to expel a therapeutic substance 180 out of the needle 50 and toward a target site 215, the needle 50 may simultaneously retract 202 in a proximal direction out of the cavity 211. Without wishing to be bound by theory, withdrawal of the needle during expelling of therapeutic substance from the needle may create a volume of space for the therapeutic substance to occupy, and may help to reduce backflow of the therapeutic substance out of the target site 215.

According to one aspect, the delivery device may be configured to help reduce cell settling or particle settling within the needle lumen. In some embodiments, the diameter of the needle lumen is less than 1 mm. In some embodiments, the ratio of the needle lumen diameter to the cell or particle diameter is less than 100:1.

According to one aspect, the delivery device may be configured to help a user to control the ejection rate of the therapeutic substance. With some therapeutic substances, such as certain types of cells, a slower ejection rate may help to reduce shear or other harmful effects on the cells, which may result in a higher viability of cells delivered. A slower ejection rate may also reduce the risk of brain tissue trauma. In some embodiments, the device actuator is a rotary actuator. In some embodiments, multiple complete turns of the rotary actuator are needed to deliver a total target volume.

According to one aspect, the delivery device may be configured to improve dose assurance. In some embodiments, the therapeutic substance is contained in a needle lumen that is relatively small and has a constant diameter. In the case of cells, such an arrangement may help the cells to move in tandem with its fluid solution, which may help to ensure delivery of a larger portion of the cells. In some embodiments, such an arrangement may help to reduce cell settling.

According to one aspect, the delivery device may be configured to help reduce waste of the therapeutic substance that may arise during loading of the substance into the delivery device. The inventors have appreciated that, with some delivery devices in which substances are back-loaded, a portion of the substance may be lost due to the long travel distance required from the loading end of the device to the ejection end of the device. The inventors have recognized that front-loading a delivery device instead may help to reduce waste of the therapeutic substance. Thus, in some embodiments, the delivery device is configured to be front-loaded with the therapeutic substance. In some embodiments, the delivery device may include an air vent arrangement to permit front-loading. In some embodiments, the delivery device may include an arrangement for priming the system after the therapeutic substance has been loaded to remove air from the delivery device prior to use, to prevent injection of air into the target site.

According to one aspect, the delivery device may include an indicator comprising only mechanical components. Such an arrangement may permit the delivery device to be more portable and easier to sterilize due to a lack of electrical components.

According to one aspect, the delivery device is used with a stereotactic frame, e.g. for neurosurgery applications. In some embodiments, the delivery device may be sized and shaped to be compatible with existing stereotactic frames.

Figure 3A:
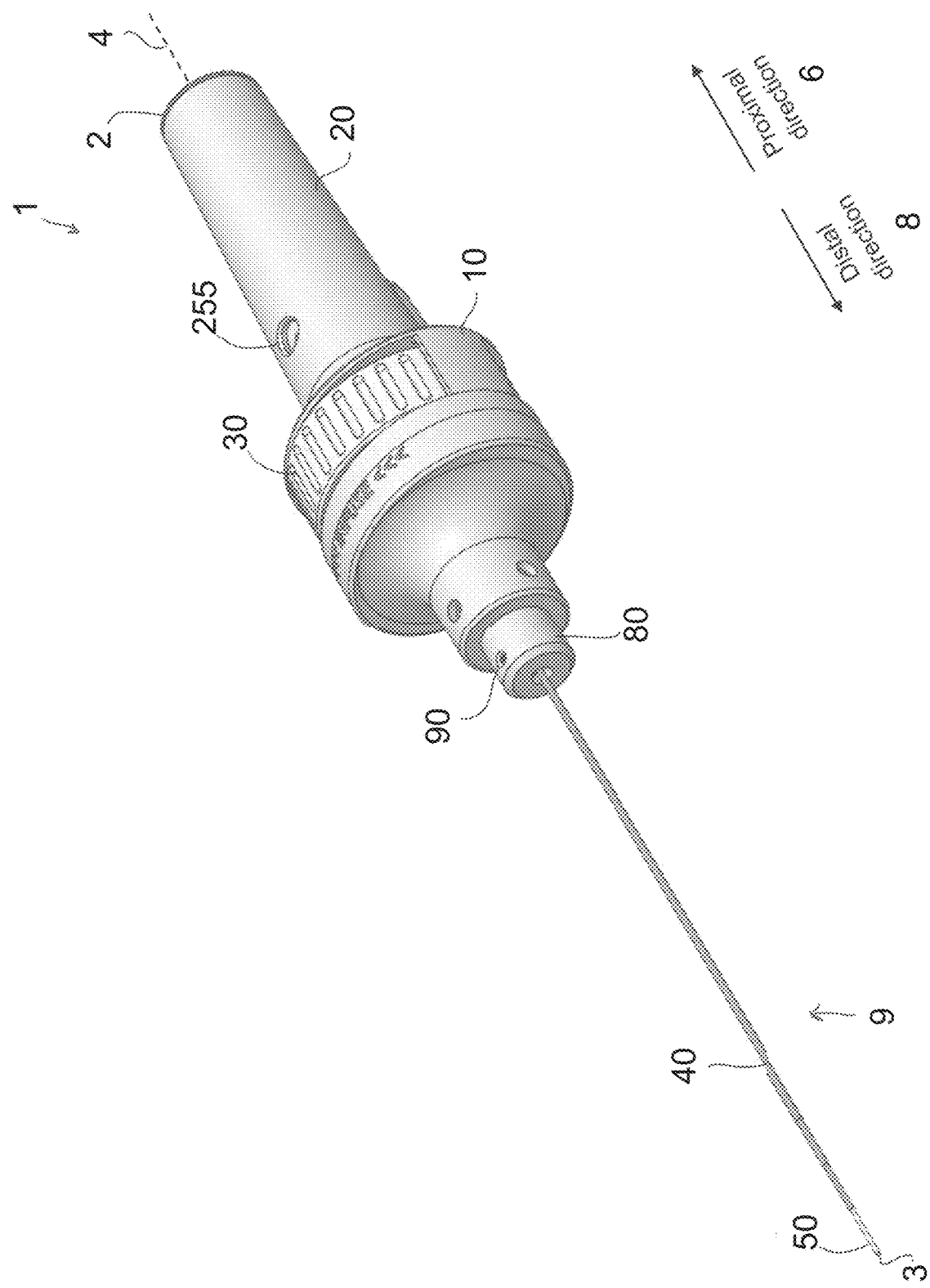
FIG. 3A is a perspective view of one embodiment of a delivery device.
Figure 3B:
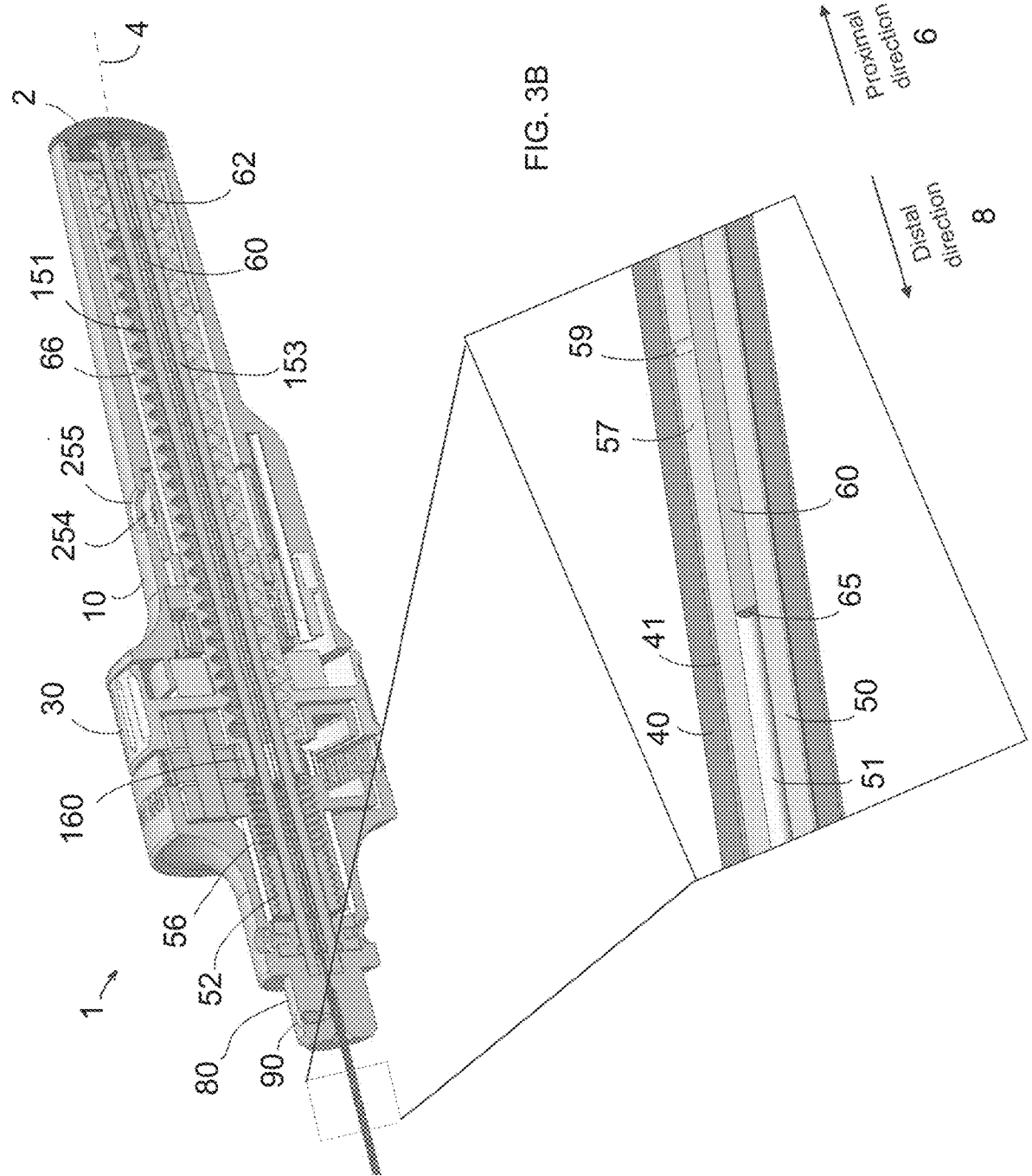
FIG. 3B is a partial cutaway view of one embodiment of the delivery device of FIG. 3A, with a detailed view of a cannula portion of the delivery device.

Turning to the illustrative embodiments in the figures, FIG. 3A is a perspective view of one embodiment of a delivery device 1, and a partial cutaway view with the internal components of the delivery device is shown in FIG. 3B. The delivery device has a cannula portion 9 through which substances are ejected, a housing 10, a handle 20, and a device actuator 30. As seen in the detailed view of FIG. 3B, the cannula portion 9 may include a plurality of components that are sheathed within one another. Moving from the outermost component of the cannula portion 9 to the innermost component, the cannula portion 9 may include an outer shaft 40, a needle 50 within the outer shaft 40, and a plunger 60 within the needle 50.

The outer shaft 40 has a shaft lumen 41 through which the needle 50 is moveable. The needle 50 has a needle lumen 51 through which the plunger 60 is moveable. Actuation of the device actuator 30 may cause the plunger 60 to move through the shaft lumen 41 in a distal direction 8. When a therapeutic substance is loaded within the needle lumen 51, movement of the plunger 60 through the needle lumen 51 in the distal direction 8 positively displaces the therapeutic substance out of the needle lumen 51, thus delivering the therapeutic substance.

As seen in FIG. 3A, the outer shaft 40 can include a plurality of segments having stepped outer diameters arranged sequentially along the longitudinal axis 4 of the device. The stepped outer diameters of the plurality of segments increase from a distal end of the outer shaft 40 towards a proximal end of the outer shaft 40 along the longitudinal axis 4 of the device. In one embodiment, one of the plurality of segments may have a first outer diameter or a first range of outer diameters. Further, another of the plurality of segments adjacent to and arranged proximally of the one of the plurality of segments may have a second outer diameter or a second range of outer diameters, wherein the second outer diameter is greater than the first outer diameter and the second range of outer diameters is greater than and does not overlap with the first range of outer diameters. Still further, the outer shaft 40 may include an end face defining a step between the one of the plurality of segments and the another of the plurality of segments. The end face may project radially outwardly from the longitudinal axis 4 of the device. Alternatively, the end face may be formed as a chamfered surface that projects at an angle that is less than 90 degrees from the longitudinal axis 4 of the device in a proximal direction of the device.

The outer shaft 40 may be formed of a material such as stainless steel. Other materials may be used to form the outer shaft 40. For example, the outer shaft 40 may be formed of a MRI-compatible material such as ceramic, glass or rigid polymers. The outer shaft 40 may also be formed of material that is not MRI-compatible if such compatibility is not needed during use of the device and/or if other factors such as cost and reusability are prioritized.

Figure 4A:
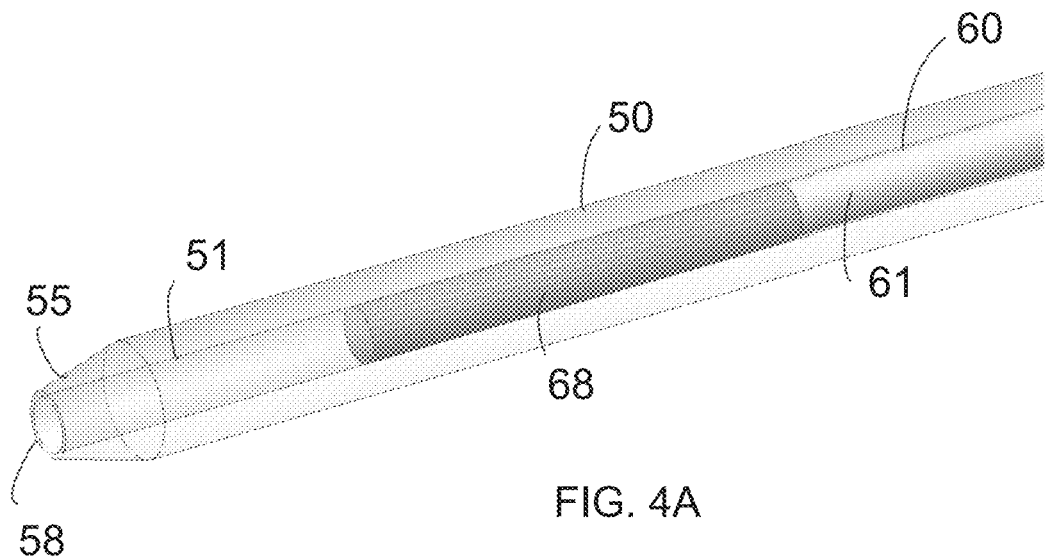
FIG. 4A is a perspective view of a needle of a delivery device, with the needle shown in phantom to show a plunger of the delivery device.

As seen in FIG. 4A, which depicts a distal portion of the needle 50 and plunger 60, the needle 50 includes a needle tip 55 defining a needle opening 58 through which the therapeutic substance is expelled. The needle tip 55 may be formed to have a chamfered outer surface that connects a plane including the needle opening 58 and a portion of the needle 50 proximal to the needle tip 55 along the longitudinal axis 4 of the device. The needle 50 may be formed of a material such as stainless steel, glass, ceramic or rigid polymers.

Figure 4B:
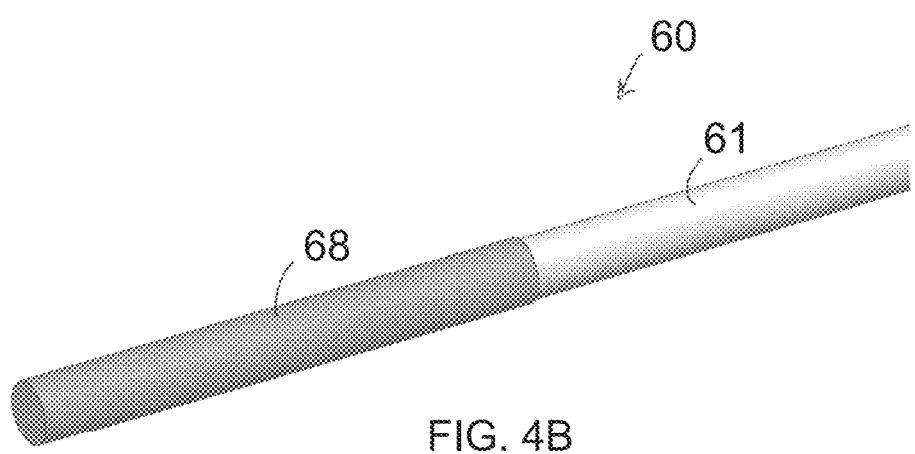
FIG. 4B is a schematic view of the plunger of FIG. 4A having a plunger seal.
Figure 4C:
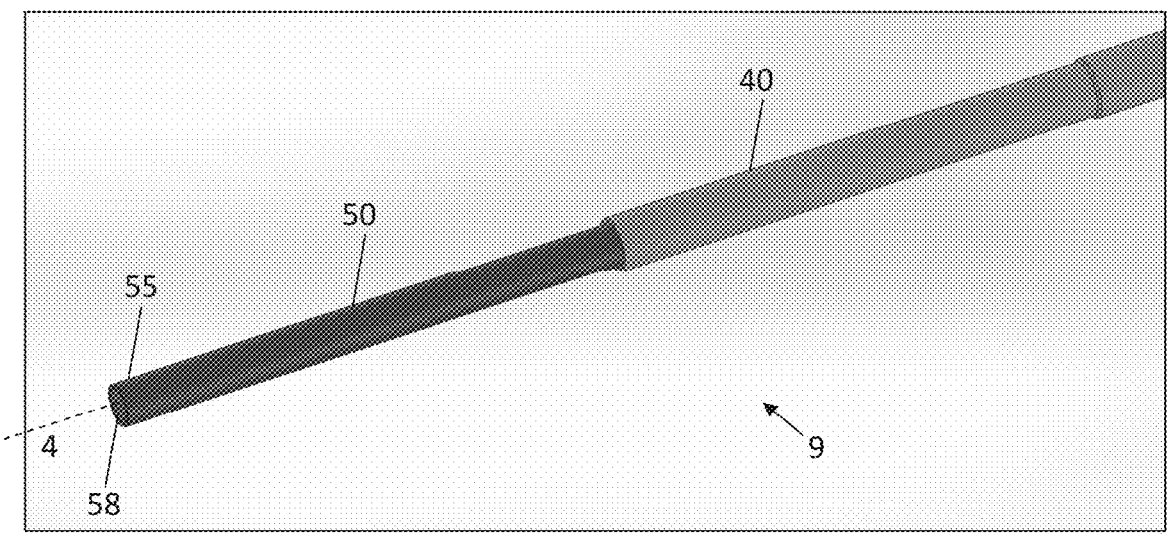
FIG. 4C is a perspective view of a needle of another embodiment of a delivery device retractably arranged inside a cannula portion of the delivery device.
Figure 4D:
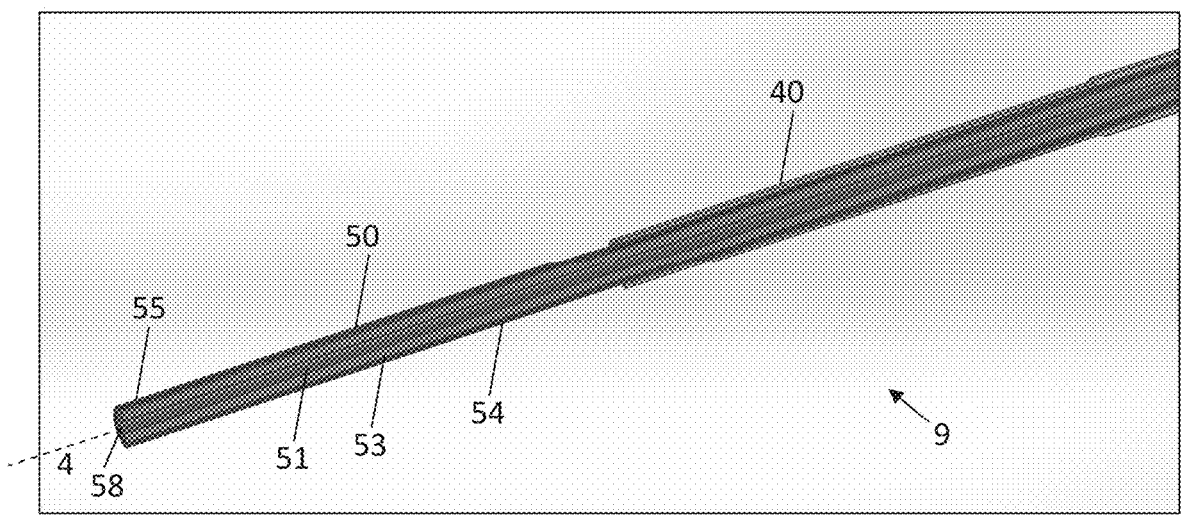
FIG. 4D is a cutaway view of the needle of FIG. 4C.

FIG. 4C is a perspective view of the needle 50 according to another embodiment. FIG. 4D is a cutaway view of the needle 50. The needle tip 55 of the needle 50 may be formed to have a flat end face that defines the needle opening 58. The flat end face may be arranged on a plane that is orthogonal to the longitudinal axis 4 of the device. Although not depicted in FIGS. 4C and 4D, the end face may be arranged on a plane that forms an angle that is not orthogonal to the longitudinal axis 4 of the device. Alternatively, the needle tip 55 may be formed to have a chamfered outer surface as shown in FIG. 4A.

As seen in FIG. 4D, the needle 50 can include a needle tube 53 that defines the needle lumen 51. The needle tube 53 can be formed of a material such as stainless steel, glass, ceramic or rigid polymers. More specifically, the needle tube 53 can be formed of a material such as polymide-coated glass. The needle 50 can further include a ferrule 54 attached to a portion of the needle tube 53. The ferrule 54 can be attached to the portion of the needle tube 53 by adhesive or other means. The ferrule 54 can be formed of a material selected to strengthen the portion of the needle tube 53 to which the ferrule 54 is attached. As an example, the ferrule 54 can be formed of a material such as stainless steel. FIG. 4D depicts the ferrule 54 being attached to a portion of the needle tube 53 that extends along the longitudinal axis 4 from the distal most end of the needle tube 53 to a proximal part of the needle tube 53. The ferrule 54 can also be attached to a portion of the needle tube 53 that extends along the longitudinal axis 4 from a first part of the needle tube 53 proximal to the distal end of the needle tube 53 to a second part of the needle tube 53 proximal to the first part. A length of the ferrule 54 along the longitudinal axis 4 may be selected to be longer than a maximum length of a portion of the needle tube 53 that can be extended distally along the longitudinal axis 4 out of the shaft lumen 41 and past the opening of the outer shaft 40 to strengthen the portion of the needle tube 53.

As seen in FIGS. 4A and 4B, the plunger 60 includes a plunger seal 68 that provides a seal against the needle lumen 51, while permitting movement of the plunger 60 through the needle lumen 51. In some embodiments, the plunger seal 68 has an outer diameter that is larger than an outer diameter of the rest of the plunger body 61. A length of the plunger seal 68 can be selected to ensure that therapeutic substance loaded in a portion of the needle lumen 51 between the needle opening 58 and a distal end of the plunger seal 68 does not travel proximally past the plunger seal 68 into another portion of the needle lumen 51 proximal of the plunger seal 68. Further, a length of the plunger seal 68 can be selected such that the plunger seal 68 acts to close a vent 59 provided in a wall 57 of the needle 50 when the plunger 60 is advanced to its distal most position within the needle lumen 51. Such a length of the plunger seal 68 is selected to ensure that as the distal end of the plunger 60 is advanced past the vent 59 the vent 59 remains closed by the plunger seal 68 to prevent a liquid from entering the needle lumen 51 through the vent 59 and traveling past the plunger seal 68 into a portion of the needle lumen 51 distal of the plunger seal 68, and to prevent a liquid in a portion of the needle lumen 51 distal of the plunger seal 68 from traveling past the plunger seal 68 and entering a portion of the needle lumen 51 proximal of the plunger seal 68.

In some embodiments, a distal portion of the plunger body 61 may be sheathed within the plunger seal 68. The plunger seal 68 can be formed as a heat shrink seal on the plunger body 61. The plunger seal 68 can also be formed as a coating of polymer through deposition or coating techniques. In other embodiments, the plunger body 61 is not sheathed within the plunger seal 68, but the two components are connected together. In still other embodiments, the plunger body 61 and the plunger seal 68 are formed as a single body.

According to one aspect, the needle may be arranged to retract while therapeutic substance is ejected from the needle. In some embodiments, during use, the needle is inserted into tissue to reach a desired target location. Insertion of the needle may create a cavity in the tissue. As the therapeutic substance is ejected from the needle, the needle is simultaneously retracted, thereby providing a volume of space for the therapeutic substance to inhabit. The inventors have appreciated that such an arrangement may help to reduce backflow of the therapeutic substance out of the target site back through the channel formed by the delivery device in the tissue.

In embodiments in which the delivery device uses a positive displacement delivery arrangement, e.g. a plunger that moves distally through a needle lumen to expel a therapeutic substance from the needle, the needle and the plunger may move simultaneously in opposite directions in response to actuation of the device actuator. That is, actuation of the device actuator may cause the needle to retract in a proximal direction while the plunger advances in a distal direction.

As used herein, the distal end of the delivery device is the end through which the therapeutic substance is delivered. The proximal end of the delivery device is the end of the device that is opposite to the distal end. As an illustrative example, FIG. 3A depicts a proximal end 2 and a distal end 3 of the delivery device 1.

As used herein, the proximal direction is a direction that points from the distal end of the delivery device toward the proximal end. The distal direction is a direction that points from the proximal end of the delivery device toward the distal end. As an illustrative example, FIG. 3A depicts a proximal direction 6 and a distal direction 8.

In some embodiments, actuation of the device actuator 30 causes the plunger 60 to advance in a distal direction 8, and the needle 50 to simultaneously retract in a proximal direction 6. In some embodiments, simultaneous motion of the plunger and the needle in opposite directions is achieved via an arrangement of translational screws mounted within threaded passages having oppositely oriented threads.

As shown in FIG. 3B, the delivery device 1 may include a needle translation screw 52 that is attached to the needle 50, and a plunger translation screw 62 that is attached to the plunger 60. The needle translation screw 52 is mounted within a first threaded passage 56, and the plunger translation screw 62 is mounted within a second threaded passage 66. The threads of the first threaded passage 56 are directed in an orientation opposite to an orientation of the threads of the second threaded passage 66. For example, the first threaded passage 56 may have a right-handed thread, while the second threaded passage 66 may have a left-handed thread, or vice versa. Actuation of the device actuator 30 may impart rotation to each of the first threaded passage 56 and the second threaded passage 66.

Figure 5:
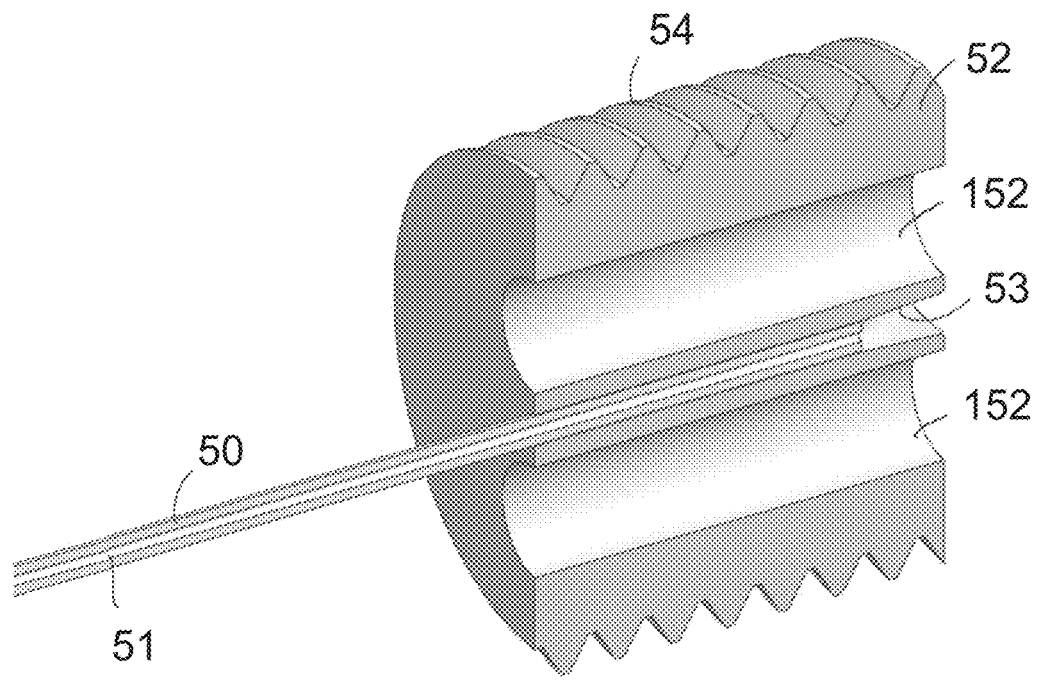
FIG. 5 is a partial cutaway view of a needle translation screw of one embodiment of a delivery device connected to a needle.
Figure 6:
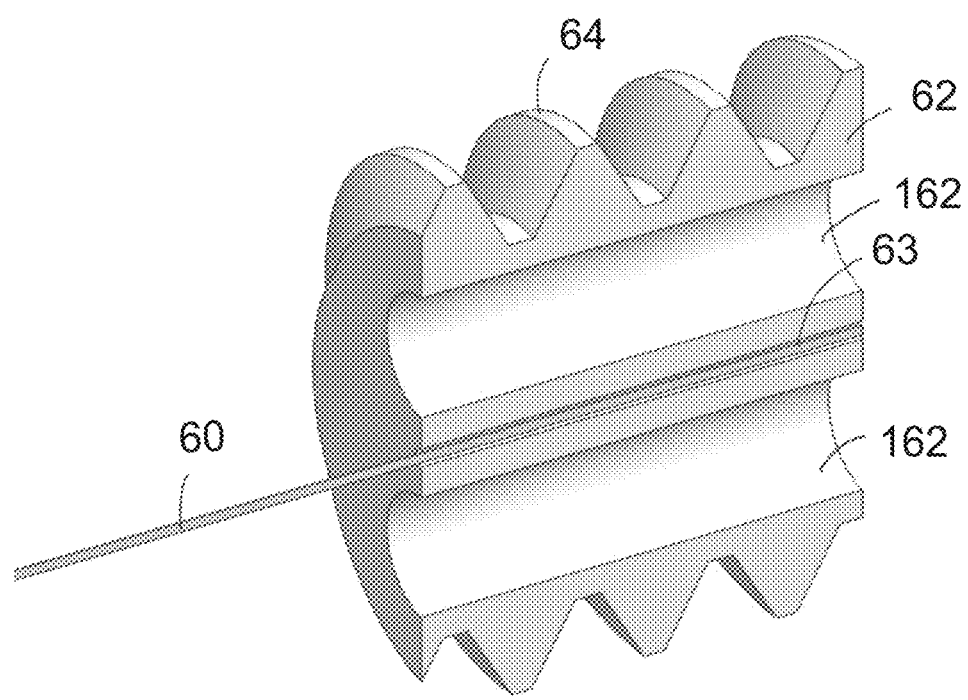
FIG. 6 is a partial cutaway view of a plunger translation screw of one embodiment of a delivery device connected to a plunger.

As shown in FIG. 3B, the needle translation screw 52 and the plunger translation screw 62 may be mounted to guide rails 151, 153. The guide rails may extend through the delivery device 1 in a direction parallel to the longitudinal axis 4 of the device, and may be fixed relative to the housing 10. As shown in FIG. 5, the needle translation screw 52 may include guide rail lumens 152 through which the guide rails 151, 153 pass. The needle translation screw 52 may be free to translate linearly along the guide rails 151, 153. As shown in FIG. 6, the plunger translation screw 62 may include guide rail lumens 162 through which the guide rails 151, 153 pass. The plunger translation screw 62 may be free to translate linearly along the guide rails 151, 153.

The guide rails 151, 153 prevent the needle translation screw 52 from rotating with the first threaded passage 56 as the first threaded passage rotates. As a result, due to the direction of the threads in the first threaded passage 56, and due to the presence of the guide rails passing through the needle translation screw 52, rotation of the first threaded passage 56 causes the needle translation screw 52 to translate through the first threaded passage 56. In the illustrative embodiment of FIG. 3B, the needle translation screw 52 moves in the proximal direction 6 when the device actuator 30 is actuated. With the needle 50 attached to the needle translation screw 52, proximal movement of the needle translation screw 52 moves the needle 50 in the proximal direction 6, thus causing the needle to retract.

Similarly, the guide rails 151, 153 prevent the plunger translation screw 62 from rotating with the second threaded passage 66 as the second threaded passage rotates. As a result, due to the direction of the threads in the second threaded passage 66, and due to the presence of the guide rails passing through the plunger translation screw 62, rotation of the second threaded passage 66 causes the plunger translation screw 62 to translate through the second threaded passage 66. In the illustrative embodiment of FIG. 3B, the plunger translation screw 62 moves in the distal direction 8 when the device actuator 30 is actuated. With the plunger 60 attached to the plunger translation screw 62, distal movement of the plunger translation screw 62 moves the plunger in the distal direction 8, thereby expelling the therapeutic substance out of the needle opening.

As shown in more detail in FIG. 5, the needle 50 is connected to the needle translation screw 52. The needle 50 may extend at least partially into the screw lumen 53. The needle 50 may attach to the needle translational screw 52 via any suitable arrangement, such as adhesive, e.g., epoxy or UV adhesive, mechanical interlock, interference fit, welding the components together, or the needle 50 and the needle translational screw 52 may be integrally formed with one another.

As used herein, parts that are "integrally formed" with one another means that the parts are formed as one component such that they are formed from a single monolithic component, e.g., cast at the same time as a single piece such as in die casting or injection molding, or cut from a single material such as in stamping or die cutting.

As shown in more detail in FIG. 6, the plunger 60 is connected to the plunger translational screw 62. The plunger 60 may extend at least partially into the screw lumen 63. The plunger 60 may attach to the plunger translational screw 62 via any suitable arrangement as discussed above with regard to the needle 50 and needle translational screw 52.

In some embodiments, the needle 50 and the needle translational screw 52 attached to the needle 50 and/or the plunger 60 and the plunger translational screw 62 attached to the plunger 60 can be removed from the housing 10 and replaced by another needle and another needle translational screw attached to the another needle and/or another plunger and another plunger translational screw attached to the another plunger. The another needle and the another needle translational screw can be arranged in the housing 10 to be translated through the first threaded passage 56, and the another plunger and the another plunger translational screw can be arranged in the housing 10 to be translated through the second threaded passage 66. The another needle can be a replacement for the needle 50 and have similar physical dimensions (e.g., same sized needle lumen) and similar functions (e.g., same amount of travel permitted) as the needle 50. Alternatively, the another needle can have different physical dimensions (e.g., different sized needle lumen) and different functions (e.g., different amount of travel permitted) as the needle 50.

Figure 7A:
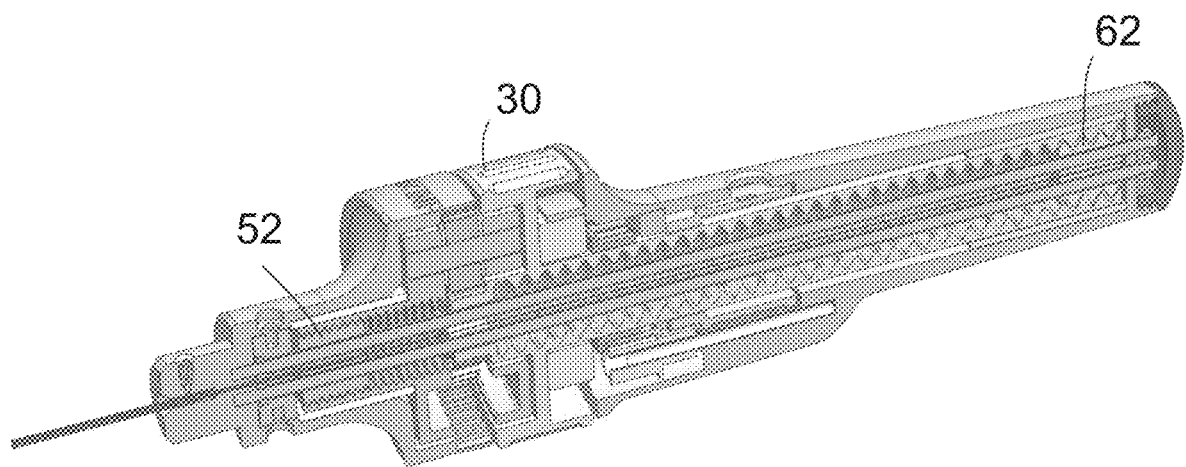
FIG. 7A is a partial cutaway view of the delivery device of FIG. 3A in a pre-delivery configuration.
Figure 7B:
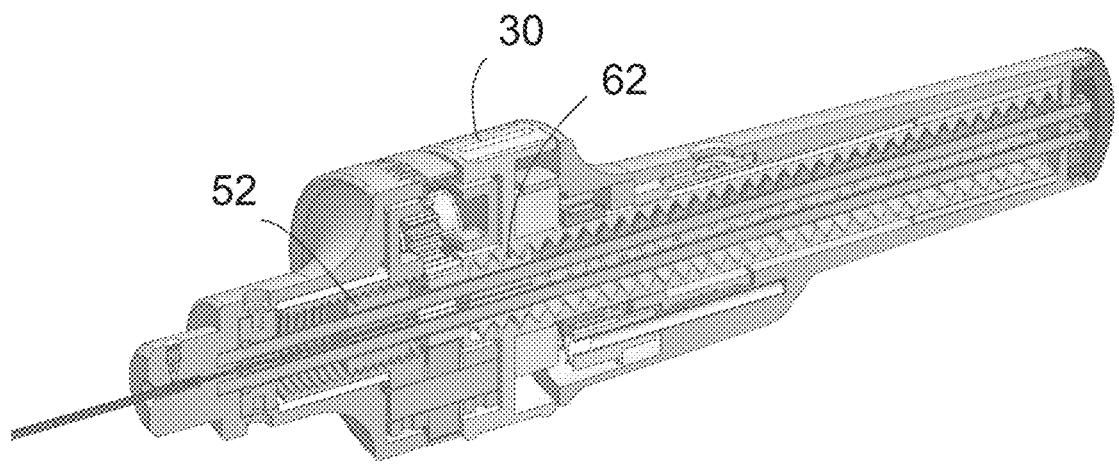
FIG. 7B is the delivery device of FIG. 7A in a post-delivery configuration.

FIG. 7A shows the delivery device in a pre-delivery configuration, and FIG. 7B shows the delivery device in a post-delivery configuration. At the end of delivery, the needle translational screw 52 has translated through the first threaded passage 56 in the proximal direction 6, thereby retracting the needle, and the plunger translational screw 62 has translated through the second threaded passage 66 in the distal direction 8, thereby advancing the plunger in the deployment direction.

In some embodiments, after delivery into the volume of space in the tissue created by the needle, the therapeutic substance occupies a portion of the volume of space. In some embodiments, the therapeutic substance occupies a therapeutic substance volume that is within at least about 5%, 10%, 15%, 20%, 25%, 30%, 40%, 50%, or 60% of the volume of space. In some embodiments, the therapeutic substance occupies a therapeutic substance volume that is within less than or equal to about 70%, 60%, 50%, 40%, 30%, 25%, 20%, 15%, 10%, or 5% of the volume of space. Combinations of the above-referenced ranges are also possible. In some embodiments, the therapeutic substance occupies a therapeutic substance volume that is within about 5% to about 60%, about 5% to about 50%, about 5% to about 40%, about 5% to about 30%, or about 5% to about 25% of the volume of space.

According to one aspect, the diameter of the needle lumen is dimensioned for compatibility with the properties of the therapeutic substance. In some embodiments, the therapeutic substance includes cells or other particles having a certain diameter. According to one aspect, the diameter of the needle lumen is close in size to the diameter of the cells or particles of the therapeutic substance. For example, in some embodiments, the ratio of the needle lumen diameter to the cell or particle diameter is less than 100:1. In some embodiments, such an arrangement may help to reduce cell settling or particle settling within the needle lumen. In some embodiments, such an arrangement may help the cells to move in tandem with its fluid solution, which may help to ensure delivery of a larger portion of the cells. Such an arrangement may help to improve dose assurance.

In some embodiments, the delivery device is configured to deliver cells that are neural cells. In some embodiments, the cells are dopaminergic neuron cells, and, in some embodiments, may be iPSC-derived dopaminergic neuron cells. It should be appreciated however, that the delivery device may be used to deliver other type of cells, such as mesenchymal stem cells, hematopoietic stem cells, embryonic stem cells or induced pluripotent stem cells, red blood cells, platelets, chondrocytes, skin cells, immune cells (e.g. tumor infiltrating lymphocytes, viral reconstitution T cells, dendritic cells, regulator T cells, macrophages), neural crest stem cells, neurons, glia, smooth muscle, cardiac tissue, chondrocytes, osteocytes, glial restricted progenitors, astrocytes, oligodendrocytes, neuroblast cells, megakaryoblasts, megakaryocytes, monoblasts, monocytes, macrophages, myeloid dendritic cells, proerythroblasts, erythroblasts, normoblasts, reticulocytes, thrombocytes, myeloblasts, progranulocytes, neutrophilic myelocytes, neutrophilic band cells, neutrophils, eosinophilic myelocytes, eosinophilic band cells, eosinophils, basophilic myelocytes, basophilic band cells, basophils, committed lymphoid projenitors, pre-NK cells, NK lymphoblasts, NK cells, thymocytes, T-lymphoblasts, T-cells, plasmacytoid dendritic cells, pre-B cells, B-lymphoblasts, B cells, plasma cells, osteoblasts, chondrocytes, myoblasts, myotubes, fibroblasts, adipocytes, mesoderm, ectoderms, primordial germ cells, sperm, eggs, definitive endoderm, or any other suitable type of cell.

In some embodiments, the therapeutic substance contains a cell concentration of at least about 50,000 cells/µL, at least about 100,000 cells/µL, at least about 200,000 cells/µL, at least about 300,000 cells/µL, at least about 400,000 cells/µL, or at least about 500,000 cells/µL. In some embodiments, the therapeutic substance contains a cell concentration of less than or equal to about 500,000 cells/µL, less than or equal to about 400,000 cells/µL, less than or equal to about 300,000 cells/µL, less than or equal to about 200,000 cells/µL, less than or equal to about 100,000 cells/µL, or less than or equal to about 50,000 cells/µL. Combinations of the above-referenced ranges are also possible. For example, in some embodiments, the therapeutic substance contains a cell concentration of about 50,000 cells/µL to about 500,000 cells/µL, or about 100,000 cells/µL to about 400,000 cells/µL, about 200,000 cells/µL to about 300,000 cells/µL.

In some embodiments, the needle lumen may have a diameter of at least about 0.05 mm, at least about 0.1 mm, at least about 0.15 mm, at least about 0.2 mm, at least about 0.25 mm, at least about 0.3 mm, at least about 0.35 mm, at least about 0.4 mm, at least about 0.45 mm, or at least about 0.5 mm. In some embodiments, the needle lumen may have a diameter of less than or equal to about 1 mm, less than or equal to about 0.95 mm, less than or equal to about 0.9 mm, less than or equal to about 0.85 mm, less than or equal to about 0.8 mm, less than or equal to about 0.75 mm, less than or equal to about 0.7 mm, less than or equal to about 0.65 mm, less than or equal to about 0.6 mm, less than or equal to about 0.55 mm, less than or equal to about 0.5 mm, less than or equal to about 0.45 mm, less than or equal to about 0.4 mm, less than or equal to about 0.35 mm, less than or equal to about 0.3 mm, less than or equal to about 0.25 mm, less than or equal to about 0.2 mm, less than or equal to about 0.15 mm, or less than or equal to about 0.1 mm. Combinations of the above-referenced ranges are also possible. For example, in some embodiments, the needle lumen may have a diameter of about 0.1 mm to about 1 mm, or about 0.15 mm to about 0.9 mm, or about 0.2 mm to about 0.8 mm, or about 0.2 mm to about 0.7 mm, or about 0.2 mm to about 0.6 mm, or about 0.2 mm to about 0.5 mm, or about 0.2 mm to about 0.4 mm, or about 0.25 mm to about 0.3 mm.

In some embodiments, the cells or particles of the therapeutic substance may have a diameter of at least about 400 nm, at least about 1 micron, at least about 2 microns, at least about 4 microns, at least about 6 microns, at least about 8 microns, at least about 9 microns, at least about 10 microns, at least about 11 microns, at least about 12 microns, at least about 13 microns, at least about 14 microns, at least about 15 microns, at least about 16 microns, at least about 17 microns, at least about 18 microns, at least about 19 microns, at least about 20 microns, at least about 25 microns, at least about 30 microns, at least about 40 microns, at least about 50 microns, at least about 70 microns, at least about 100 microns, at least about 200 microns, or at least about 500 microns. In some embodiments, the cells or particles may have a diameter of less than or equal to about 500 microns, less than or equal to about 300 microns, less than or equal to about 200 microns, less than or equal to about 150 microns, less than or equal to about 100 microns, less than or equal to about 90 microns, less than or equal to about 80 microns, less than or equal to about 70 microns, less than or equal to about 60 microns, less than or equal to about 50 microns, less than or equal to about 40 microns, less than or equal to about 30 microns, less than or equal to about 20 microns, less than or equal to about 19 microns, less than or equal to about 18 microns, less than or equal to about 17 microns, less than or equal to about 16 microns, less than or equal to about 15 microns, less than or equal to about 14 microns, less than or equal to about 13 microns, less than or equal to about 12 microns, less than or equal to about 11 microns, less than or equal to about 10 microns, less than or equal to about 9 microns, less than or equal to about 8 microns, less than or equal to about 7 microns, less than or equal to about 6 microns, less than or equal to about 5 microns, less than or equal to about 4 microns, less than or equal to about 2 microns, or less than or equal to about 1 micron. Combinations of the above-referenced ranges are also possible. For example, in some embodiments, the cells or particles may have a diameter of about 400 nm to about 500 microns, or about 1 micron to about 200 microns, or about 5 microns to about 150 microns, or about 8 microns to about 120 microns, or about 8 microns to about 100 microns, or about 8 microns to about 50 microns, or about 8 microns to about 40 microns, or about 8 microns to about 30 microns, or about 8 microns to about 20 microns, or about 10 microns to about 15 microns.

In some embodiments, the ratio of the needle lumen diameter to the cell or particle diameter is at least about 10:1, 20:1, 30:1, 40:1, 50:1, 60:1, 70:1, 80:1, 90:1, 100:1, 150:1, 200:1, 300:1, 400:1 or 500:1. In some embodiments, the ratio of the needle lumen diameter to the cell or particle diameter is less than or equal to about 500:1, 400:1, 300:1, 200:1, 100:1, 90:1, 80:1, 70:1, 60:1, 50:1, 40:1, 30:1, 20:1 or 10:1. Combinations of the above-referenced ranges are also possible. For example, in some embodiments, the ratio of the needle lumen diameter to the cell or particle diameter is about 10:1 to about 500:1, or about 50:1 to about 300:1, or about 60:1 to about 200:1, or about 70:1 to about 150:1, or about 80:1 to about 120:1, or about 90:1 to about 110:1.

In some embodiments, the entire volume of the therapeutic substance that is loaded into the delivery device is contained only in the needle lumen of the delivery device. In some embodiments, the needle lumen has a constant diameter along the entire length of the needle. In the case of cells, such an arrangement may help the cells to move in tandem with its fluid solution, which may help to ensure delivery of a larger portion of the cells. Such an arrangement may help to improve dose assurance. In some embodiments, such an arrangement may help to reduce cell settling.

In some embodiments, the density of the fluid solution in which the cells and/or particles are provided is selected to increase the buoyancy force exerted on the cells and/or particles. For example, the density of the fluid solution can be selected in view of a known density of the cells and/or particles to be delivered to approach the known density to increase the buoyancy force exerted on the cells and/or particles to achieve or approach neutral buoyancy. Further, the density of the fluid solution can be selected in view of the known density of the cells and/or particles to be delivered to approach the known density to thereby increase the buoyancy force exerted on the cells and/or particles such that a cell and/or particle concentration of the fluid solution ejected by the delivery device approaches a predetermined concentration. In other embodiments, the viscosity of the fluid solution can be selected to reduce cell settling such that a cell and/or particle concentration of the fluid solution ejected by the delivery device approaches a predetermined concentration. In yet other embodiments, the density of the fluid solution and the viscosity of the fluid solution can both be selected in the above-described manner. Such arrangements may further help to reduce cell settling.

According to one aspect, the volume of space through which the plunger moves in response to device actuation (and/or the volume of therapeutic substance ejected by the delivery device) is close to or substantially the same as the volume of space through which the needle moves during retraction of the needle. In some embodiments, the volume of space through which the plunger moves (and/or the volume of therapeutic substance ejected by the delivery device) is within at least 1, 2, 3, 4, 5, 6, 7, 8, 9, 10, 11, 12, 13, 14, 15, 16, 17, 18, 19, 20, 25, 30, 40, or 50 percent of the volume of space through which the needle moves. In some embodiments, the volume of space through which the plunger moves (and/or the volume of therapeutic substance ejected by the delivery device) is within less than or equal to 50, 40, 30, 25, 20, 19, 18, 17, 16, 15, 14, 13, 12, 11, 10, 9, 8, 7, 6, 5, 4, 3, 2, 1 percent of the volume of space through which the needle moves. Combinations of the above-referenced ranges are also possible. In some embodiments, the volume of space through which the plunger moves (and/or the volume of therapeutic substance ejected by the delivery device) is within 1 to 50, 1 to 40, 1 to 30, 1 to 25, 1 to 20, 1 to 15, 1 to 10, or 1 to 5 percent of the volume of space through which the needle moves.

The inventors have recognized that, with a positive displacement arrangement, the plunger travel distance may determine the delivery volume. However, in embodiments where the needle retracts as the plunger advances, the inventors have appreciated that the needle travel distance may not necessarily match the plunger travel distance in all embodiments. In some embodiments, the needle travel distance may be determined by the anatomy of the target site.

According to one aspect, the needle and the plunger may undergo different travel distances during delivery. Such an arrangement may allow the plunger to travel a certain distance to deliver a desired volume of the therapeutic substance, while allowing for a travel distance of the needle that is appropriate for the target anatomy.

In some embodiments, the different travel distances of the plunger and the needle are accomplished via a difference in thread count (e.g., threads per inch) of the threaded passages associated with the translational screws, or via a gear system, or, in some embodiments, a combination of both.

In the illustrative embodiment shown in FIG. 3B, the first threaded passage 56, which is the passage along which the needle translation screw 52 translates, has a first thread count. The second threaded passage 66, which is the passage along which the plunger translation screw 62 translates, has a second thread count that is different from the first thread count. In some embodiments, such as with the embodiment shown in FIG. 3B, the needle travel distance is shorter than the plunger travel distance. To achieve this difference in travel distance, the first threaded passage 56 has a greater thread count (e.g., higher threads per inch) than the thread count of the second threaded passage 66. Accordingly, with the actuation of the device actuator 30, the plunger translation screw 62 translates a greater distance than the needle translation screw. As a result, the plunger moves a greater distance than the needle.

In some embodiments, the ratio of the first thread count to the second thread count may be at least about 1.5:1, at least about 1.6:1, at least about 1.7:1, at least about 1.8:1, at least about 1.9:1, at least about 2:1, at least about 2.1:1, at least about 2.2:1, at least about 2.3:1, at least about 2.4:1, at least about 2.5:1, at least about 2.6:1, at least about 2.7:1, at least about 2.8:1, at least about 2.9:1, at least about 3:1, at least about 3.1:1, at least about 3.2:1, at least about 3.3:1, at least about 3.4:1, at least about 3.5:1, at least about 3.6:1, at least about 3.7:1, at least about 3.8:1, at least about 3.9:1, at least about 4:1, at least about 4.2:1, at least about 4.4:1, at least about 4.6:1, at least about 4.8:1, at least about 5:1, at least about 6:1, at least about 7:1, at least about 8:1, at least about 9:1, at least about 10:1, at least about 11:1, at least about 12:1, at least about 13:1, at least about 14:1, at least about 15:1, at least about 16:1, at least about 18:1, or at least about 20 to 1. In some embodiments, the ratio of the first thread count to the second thread count may be less than or equal to about 20:1, less than or equal to about 18:1, less than or equal to about 16:1, less than or equal to about 14:1, less than or equal to about 12:1, less than or equal to about 10:1, less than or equal to about 9:1, less than or equal to about 8:1, less than or equal to about 7:1, less than or equal to about 6:1, less than or equal to about 5:1, less than or equal to about 4.5:1, less than or equal to about 4:1, less than or equal to about 3.9:1, less than or equal to about 3.8:1, less than or equal to about 3.7:1, less than or equal to about 3.6:1, less than or equal to about 3.5:1, less than or equal to about 3.4:1, less than or equal to about 3.3:1, less than or equal to about 3.2:1, less than or equal to about 3.1:1, less than or equal to about 3:1, less than or equal to about 2.9:1, less than or equal to about 2.8:1, less than or equal to about 2.7:1, less than or equal to about 2.6:1, less than or equal to about 2.5:1, less than or equal to about 2.4:1, less than or equal to about 2.3:1, less than or equal to about 2.2:1, less than or equal to about 2.1:1, less than or equal to about 2:1, less than or equal to about 1.9:1, less than or equal to about 1.8:1, less than or equal to about 1.7:1, less than or equal to about 1.6:1, or less than or equal to about 1.5:1. Combinations of the above-referenced ranges are also possible. For example, in some embodiments, the ratio of the first thread count to the second thread count may be about 1.5:1 to about 20:1, or about 1.6 to 1 to about 14:1, or about 1.7:1 to about 10:1, or about 1.8:1 to about 9:1, or about 1.9:1 to about 8:1, or about 2:1 to about 7:1, or about 2.1:1 to about 6:1, or about 2.2:1 to about 5:1, or about 2.3:1 to about 4:1, or about 2.4:1 to about 3:1 or about 2.5:1 to about 2.7:1.

Figure 8:
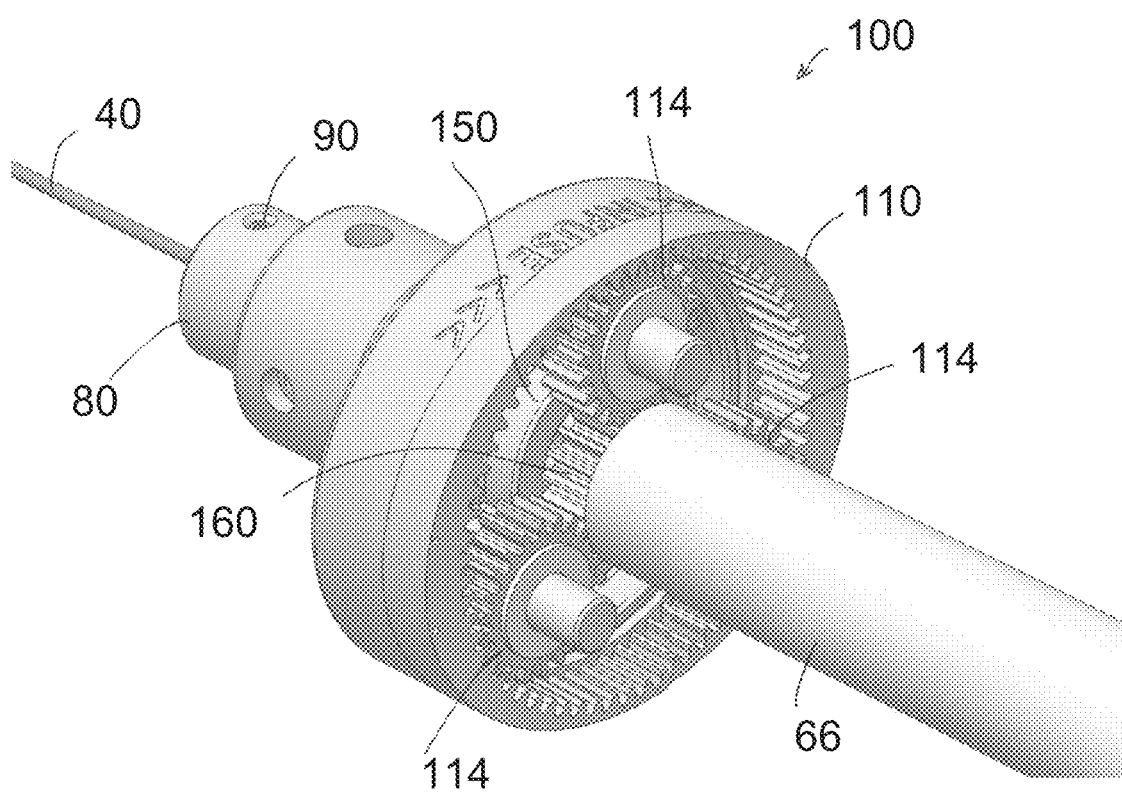
FIG. 8 is a perspective view of a planetary gear system of one embodiment of a delivery device.
Figure 9:
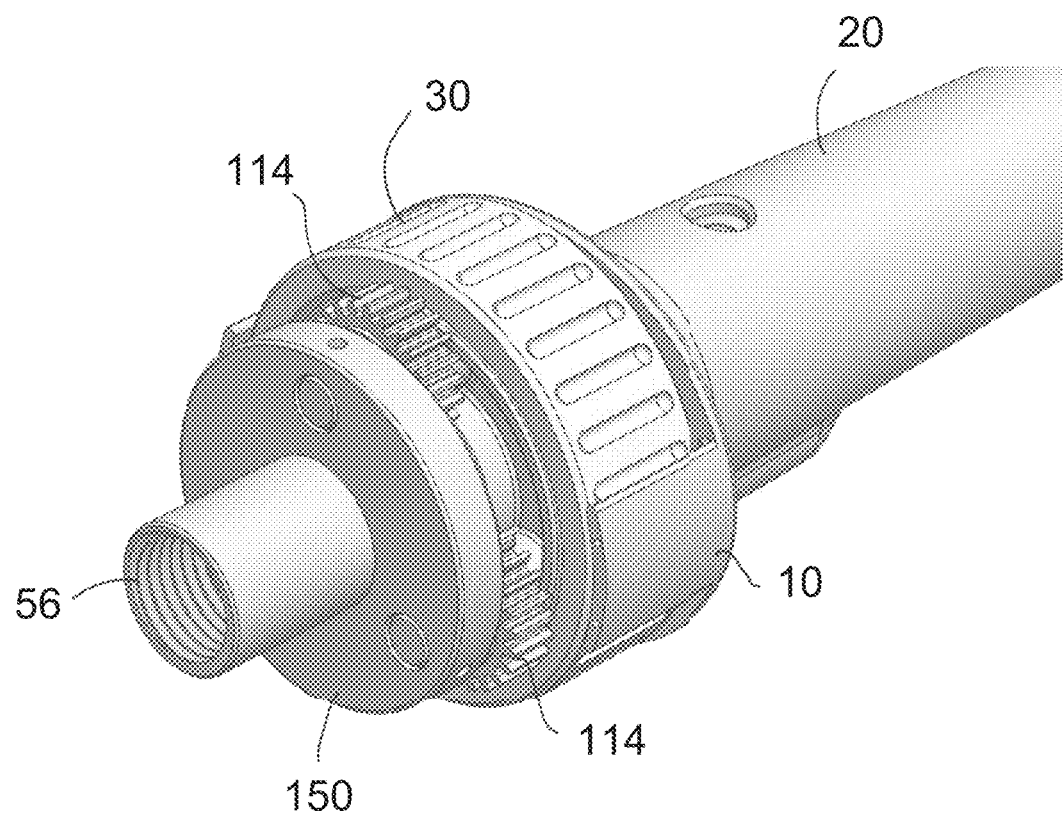
FIG. 9 is another perspective view of the planetary gear system of FIG. 8, with some components hidden from view.

In the illustrative embodiment of FIG. 3B, a gear system is additionally employed to further reduce the travel distance of the needle relative to the travel distance of the plunger. As shown in FIGS. 8 and 9, the gear system is a planetary gear system 100, (also known as an epicyclical gear system). The planetary gear system 100 includes a sun gear 160, planet gears 114, and a ring gear 110.

The sun gear 160 is connected to the device actuator 30 and the second threaded passage 66 (which is associated with the plunger translation screw). As shown in FIG. 3B, the sun gear 160, the device actuator 30, and the second threaded passage 66 are integrally formed together as a single component. One complete rotation of the device actuator 30 also results in one complete rotation of the sun gear 160 and one complete rotation of the second threaded passage 66. The planet gears 114 rotate around the sun gear 160 and within a ring gear 110. As shown in FIG. 9, the planet gears 114 are rotatably mounted to a carrier 150, and the carrier 150 is connected to the first threaded passage 56, (which is associated with the needle translation screw). One complete rotation of the carrier 150 results in one complete rotation of the first threaded passage. The relationship between the sun gear 160 and the planet gears 114 creates a gear ratio, where multiple rotations of the sun gear are required to achieve a single complete rotation of the carrier. As a result, actuation of the device actuator 30 results in more rotation of the second threaded passage 66 than the first threaded passage 56, which in turn results in a greater travel distance of the plunger translation screw 62 and the plunger 60 than that of the needle translation screw 52 and the needle 50.

In some embodiments, the gear ratio of the sun gear 160 to the carrier 150 may be at least about 2 to 1, at least about 2.5 to 1, at least about 3 to 1, at least about 3.2 to 1, at least about 3.4 to 1, at least about 3.6 to 1, at least about 3.8 to 1, at least about 4 to 1, at least about 4.1 to 1, at least about 4.2 to 1, at least about 4.3 to 1, at least about 4.4 to 1, at least about 4.5 to 1, at least about 4.6 to 1, at least about 4.7 to 1, at least about 4.8 to 1, at least about 4.9 to 1, at least about 5 to 1, at least about 6 to 1, at least about 7 to 1, at least about 8 to 1, at least about 9 to 1, or at least about 10 to 1. In some embodiments, the gear ratio of the sun gear to the carrier may be less than or equal to about 10 to 1, less than or equal to about 9 to 1, less than or equal to about 8 to 1, less than or equal to about 7 to 1, less than or equal to about 6 to 1, less than or equal to about 5 to 1, less than or equal to about 4.9 to 1, less than or equal to about 4.8 to 1, less than or equal to about 4.7 to 1, less than or equal to about 4.6 to 1, less than or equal to about 4.5 to 1, less than or equal to about 4.4 to 1, less than or equal to about 4.3 to 1, less than or equal to about 4.2 to 1, less than or equal to about 4.1 to 1, less than or equal to about 4 to 1, less than or equal to about 3.8 to 1, less than or equal to about 3.6 to 1, less than or equal to about 3.4 to 1, less than or equal to about 3.2 to 1, less than or equal to about 3 to 1, less than or equal to about 2.5 to 1, less than or equal to about 2 to 1. Combinations of the above-referenced ranges are also possible. For example, in some embodiments, the ratio of the sun gear to the carrier may be about 2 to 1 to about 10 to 1, or about 2.5 to 1 to about 9 to 1, or about 3 to 1 to about 8 to 1, or about 3.2 to 1 to about 7 to 1, or about 3.4 to 1 to about 6 to 1, or about 3.6 to 1 to about 5 to 1, or about 3.8 to 1 to about 4.8 to 1, or about 3.9 to 1 to about 4.6 to 1, or about 4 to 1 to about 4.5 to 1, or about 4.1 to 1 to about 4.4 to 1, or about 4.2 to 1 to about 4.3 to 1.

While a planetary gear is used in the delivery device shown in the figures, it should be appreciated that other types of gear systems may be used, such as spur gears, helical gears, rack and pinions, bevel gears, miter gears, worm gears, screw gears, spiral gears, hypoid gears, herringbone gears, internal gears, sawtooth gears, clock and pin gears, mutilated gears, hypocycloidal gear systems, Geneva gears, or any other suitable gear system, as this aspect is not so limited.

In the illustrative embodiment of FIG. 3B, the delivery device 1 utilizes a combination of a gear system and a pair of threaded passages with different thread counts to enable the plunger and the needle to undergo different travel distances in response to actuation of the device actuator 30. The combined arrangement gives rise to a travel distance ratio between the plunger and the needle. In other embodiments, a delivery device may utilize a pair of threaded passages, or a gear system, without combining the two.

In some embodiments, the travel distance ratio between the plunger and the needle may be at least about 2 to 1, at least about 2.5 to 1, at least about 3 to 1, at least about 3.5 to 1, at least about 4 to 1, at least about 4.5 to 1, at least about 5 to 1, at least about 5.5 to 1, at least about 6 to 1, at least about 6.5 to 1, at least about 7 to 1, at least about 7.5 to 1, at least about 8 to 1, at least about 8.5 to 1, at least about 8.7 to 1, at least about 9 to 1, at least about 9.2 to 1, at least about 9.4 to 1, at least about 9.6 to 1, at least about 9.8 to 1, at least about 10 to 1, at least about 11 to 1, at least about 12 to 1, at least about 13 to 1, at least about 14 to 1, at least about 15 to 1, at least about 16 to 1, at least about 17 to 1, at least about 18 to 1, at least about 19 to 1 or at least about 20 to 1. In some embodiments, travel distance ratio between the plunger and the needle may be less than or equal to about 20 to 1, less than or equal to about 18 to 1, less than or equal to about 16 to 1, less than or equal to about 14 to 1, less than or equal to about 12 to 1, less than or equal to about 11.8 to 1, less than or equal to about 11.6 to 1, less than or equal to about 11.4 to 1, less than or equal to about 11.2 to 1, less than or equal to about 11 to 1, less than or equal to about 10.9 to 1, less than or equal to about 10.8 to 1, less than or equal to about 10.7 to 1, less than or equal to about 10.6 to 1, less than or equal to about 10.5 to 1, less than or equal to about 10.4 to 1, less than or equal to about 10.3 to 1, less than or equal to about 10.2 to 1, 10.1 to 1, less than or equal to about 10 to 1, less than or equal to about 9.9 to 1, less than or equal to about 9.8 to 1, less than or equal to about 9.7 to 1, less than or equal to about 9.6 to 1, less than or equal to about 9.5 to 1, less than or equal to about 9.4 to 1, less than or equal to about 9.3 to 1, less than or equal to about 9.2 to 1, less than or equal to about 9.1 to 1, less than or equal to about 9 to 1, less than or equal to about 8.7 to 1, less than or equal to about 8 to 1, less than or equal to about 7 to 1, less than or equal to about 6 to 1, less than or equal to about 5 to 1, less than or equal to about 4 to 1, less than or equal to about 3 to 1, or less than or equal to about 2 to 1. Combinations of the above-referenced ranges are also possible. For example, in some embodiments, the travel distance ratio between the plunger and the needle may be about 2 to 1 to about 20 to 1, or about 3 to 1 to about 18 to 1, or about 4 to 1 to about 16 to 1, or about 5 to 1 to about 14 to 1, or about 6 to 1 to about 13 to 1, or about 7 to 1 to about 12 to 1, or about 8 to 1 to about 11 to 1, or about 9 to 1 to about 10 to 1, or about 9.1 to 1 to about 10.9 to 1, or about 9.2 to 1 to about 10.8 to 1, or about 9.3 to 1 to about 10.7 to 1, or about 9.4 to 1 to about 10.6 to 1, or about 9.5 to 1 to about 10.5 to 1, or about 9.6 to 1 to about 10.4 to 1, or about 9.7 to 1 to about 10.3 to 1, or about 9.8 to 1 to about 10.2 to 1, or about 9.9 to 1 to about 10.1 to 1, or about 10 to 1 to about 10.1 to 1, or about 7 to 1 to about 10 to 1, or about 8 to 1 to about 9 to 1.

In some embodiments, the travel distance of the plunger may be at least about 10, 20, 30, 40, 50, 60, 70, 80, 90, 100, 110, 120, 130, 140, 150, 160, 180, 200, 250 or 300 mm. In some embodiments, the travel distance of the plunger may be less than or equal to about 300, 250, 200, 180, 160, 150, 140, 130, 120, 110, 100, 90, 80, 70, 60, 50, 40, 30, 20, or 10 mm. Combinations of the above-referenced ranges are also possible. For example, in some embodiments, the travel distance of the plunger may be about 10 to 300 mm, 20 to 250 mm, 30 to 200 mm, 40 to 180 mm, 50 to 160 mm, 60 to 140 mm, 70 to 140 mm, 100 to 140 mm, or 120 to 140 mm.

According to one aspect, the device actuator of the delivery device may be a rotatable actuator. In some embodiments, a rotatable device actuator may help to slow down the ejection rate of the therapeutic substance.

In some embodiments, as seen in FIG. 3A, the device actuator 30 is rotatably mounted relative to the housing 10. In some embodiments, such as the illustrative embodiment of FIG. 3A, the rotation axis of the device actuator is parallel to a longitudinal axis 4 of the delivery device 1. In other embodiments, however, the rotation axis of the device actuator may be perpendicular to the longitudinal axis of the delivery device. In some embodiments, the longitudinal axis of the delivery device is parallel with the outer shaft, the needle, and/or the plunger of the cannula portion.

In some embodiments, multiple complete turns of device actuator are needed to deliver a total target volume. For example, with embodiments of the delivery device utilizing a positive displacement arrangement having a plunger moving through a needle, multiple complete turns of the device actuator may be needed to move the plunger from its pre-delivery position to its post-delivery position for a maximum volume to be delivered. In some embodiments, to deliver a maximum volume, the post-delivery position of the distal end 65 (see FIG. 3B) of the plunger 60 is at or near the needle opening 58 (see FIG. 4A).

In the illustrative embodiment shown in FIG. 3B, the thread count of the second threaded passage 66 may determine how far the plunger translation screw 62, and thus, the plunger 60, moves with each rotation of the device actuator 30.

In some embodiments, the thread count of the second threaded passage may be at least about 1 thread per inch (TPI), at least about 4 TPI, at least about 4.4 TPI, at least about 4.6 TPI, at least about 4.8 TPI, at least about 5 TPI, at least about 5.1 TPI, at least about 5.2 TPI, at least about 5.3 TPI, at least about 5.4 TPI, at least about 5.5 TPI, at least about 5.6 TPI, at least about 5.7 TPI, at least about 5.8 TPI, at least about 5.9 TPI, at least about 6 TPI, at least about 6.1 TPI, at least about 6.2 TPI, at least about 6.3 TPI, at least about 6.4 TPI, at least about 6.5 TPI, at least about 7 TPI, at least about 8 TPI, at least about 9 TPI, at least about 10 TPI, at least about 12 TPI, at least about 14 TPI, at least about 20 TPI, at least about 40 TPI, at least about 60 TPI, or at least about 80 TPI. In some embodiments, the thread count of the second threaded passage may be less than or equal to about 80 TPI, less than or equal to about 60 TPI, less than or equal to about 40 TPI, less than or equal to about 20 TPI, less than or equal to about 14 TPI, less than or equal to about 12 TPI, less than or equal to about 10 TPI, less than or equal to about 8 TPI, less than or equal to about 7 TPI, less than or equal to about 6.9 TPI, less than or equal to about 6.8 TPI, less than or equal to about 6.7 TPI, less than or equal to about 6.6 TPI, less than or equal to about 6.5 TPI, less than or equal to about 6.4 TPI, less than or equal to about 6.3 TPI, less than or equal to about 6.2 TPI, less than or equal to about 6.1 TPI, less than or equal to about 6 TPI, less than or equal to about 5.9 TPI, less than or equal to about 5.8 TPI, less than or equal to about 5.7 TPI, less than or equal to about 5.6 TPI, less than or equal to about 5.5 TPI, less than or equal to about 5.4 TPI, less than or equal to about 5.3 TPI, less than or equal to about 5.2 TPI, less than or equal to about 5.1 TPI, less than or equal to about 5 TPI, or less than or equal to about 4 TPI. Combinations of the above-referenced ranges are also possible. For example, in some embodiments, the thread count of the second threaded passage may be about 1 TPI to about 80 TPI, or about 4 TPI to about 14 TPI, or about 4.2 TPI to about 12 TPI, or about 4.4 TPI to about 10 TPI, or about 4.6 TPI to about 9 TPI, or about 4.8 TPI to about 8.6 TPI, or about 5 TPI to about 7 TPI, or about 5.2 TPI to about 6.8 TPI, or about 5.4 TPI to about 6.6 TPI, or about 5.6 TPI to about 6.4 TPI, or about 5.8 TPI to about 6.2 TPI, or about 5.9 TPI to about 6.1 TPI, or about 6 TPI to about 6.1 TPI.

In some embodiments, to achieve a maximum delivery volume, the device actuator is turned at least 5, 10, 12, 14, 16, 18, 20, 21, 22, 23, 24, 25, 26, 27, 28 29, 30, 31, 32, 33, 34, 35, 36, 37, 38, 39, 40, 42, 44, 46, 48, 50, 55, or 60 full rotations. In some embodiments, to deliver a maximum volume, the device actuator is turned less than or equal to 60, 50, 48, 46, 44, 42, 40, 39, 38, 37, 36, 35, 34, 33, 32, 31, 30, 29, 28, 27, 26, 25, 24, 23, 22, 22.5, 21, 20, 18, 16, 14, 12, 10, or 5 full rotations. Combinations of the above-referenced ranges are also possible. For example, In some embodiments, to deliver a maximum volume, the device actuator is turned 5 to 60, or 10 to 50, or 20 to 40, or 22 to 38, or 24 to 36, or 25 to 35, or 26 to 34, or 27 to 33, or 28 to 32, or 29 to 31, or 30 to 31, or 15 to 30 full rotations.

In other embodiments, the device actuator may be turned one full rotation or less than a full rotation to deliver a maximum delivery volume. In some embodiments, to deliver a maximum delivery volume, the device actuator is turned at least about 120, 140, 160, 180, 200, 220, 240, 260, 280, 300, 320, 340, or 360 degrees. In some embodiments, to achieve a maximum delivery volume, the device actuator is turned less than or equal to about 360, 340, 320, 300, 280, 260, 240, 220, 200, 180, 160, 140, 120, or 100 degrees. Combinations of the above-referenced ranges are also possible. For example, in some embodiments, to deliver a maximum delivery volume, the device actuator is turned about 100 to about 360 degrees, or about 120 to about 340 degrees, or about 160 to about 300 degrees, or about 200 to about 260 degrees.

In some embodiments, a maximum delivery volume may be at least about 1 microliter, at least about 2 microliters, at least about 3 microliters, at least about 4 microliters, at least about 5 microliters, at least about 6 microliters, at least about 7 microliters, at least about 7.2 microliters, at least about 7.4 microliters, at least about 7.6 microliters, at least about 7.8 microliters, at least about 8 microliters, at least about 8.1 microliters, at least about 8.2 microliters, at least about 8.3 microliters, at least about 8.4 microliters, at least about 8.5 microliters, at least about 8.6 microliters, at least about 8.7 microliters, at least about 8.8 microliters, at least about 8.9 microliters, at least about 9 microliters, at least about 9.5 microliters, at least about 10 microliters, at least about 11 microliters, at least about 12 microliters, at least about 13 microliters, at least about 14 microliters, at least about 15 microliters, at least about 20 microliters, at least about 30 microliters, at least about 100 microliters, at least about 1 mL, at least about 10 mL, at least about 100 mL, at least about 500 mL, or at least about 800 mL. In some embodiments, a maximum delivery volume may be less than or equal to about 1000 mL, less than or equal to about 800 mL, less than or equal to about 500 mL, less than or equal to about 100 mL, less than or equal to about 10 mL, less than or equal to about 1 mL, less than or equal to about 100 microliters, or less than or equal to about 100 microliters, or less than or equal to about 90 microliters, or less than or equal to about 80 microliters, or less than or equal to about 70 microliters, or less than or equal to about 60 microliters, or less than or equal to about 50 microliters, or less than or equal to about 40 microliters, or less than or equal to about 30 microliters, or less than or equal to about 20 microliters, or less than or equal to about 15 microliters, or less than or equal to about 12 microliters, or less than or equal to about 10 microliters, or less than or equal to about 9.9 microliters, or less than or equal to about 9.8 microliters, or less than or equal to about 9.7 microliters, or less than or equal to about 9.6 microliters, or less than or equal to about 9.5 microliters, or less than or equal to about 9.4 microliters, or less than or equal to about 9.3 or less than or equal to about 9.2 microliters, or less than or equal to about 9.1 microliters, or less than or equal to about 9 microliters, or less than or equal to about 8.8 microliters, or less than or equal to about 8.2 microliters, or less than or equal to about 8 microliters, or less than or equal to about 7 microliters, or less than or equal to about 6 microliters, or less than or equal to about 5 microliters. Combinations of the above referenced ranges are also possible. For example, in some embodiments, a maximum delivery volume is 1 mL to about 1000 mL, or about 10 mL to about 800 mL, or about 100 mL to about 500 mL, or about 1 microliter to about 100 microliters, or about 2 microliters to about 60 microliters, or about 3 microliters to about 30 microliters, or about 4 microliters to about 20 microliters, or about 5 microliters to about 18 microliters or about 6 microliters to about 16 microliters or about 7 microliters to about 14 microliters or about 8 microliters to about 10 microliters or about 8.5 microliters to about 9.5 microliters or about 8.9 microliters to about 9.1 microliters, or about 9 microliters to about 9.1 microliters.

While at least some of the illustrative embodiments discussed herein may be purely mechanical, it should be appreciated that, in other embodiments, a delivery device may be powered. For example, in some embodiments, the delivery device may include a motor that may be actuated by a user to advance a plunger and/or retract a needle. In some embodiments, the delivery device may be controlled remotely using wireless communication. The delivery device may have a portable power source and/or may be adapted to receive power from an electrical outlet. In some embodiments, the delivery device may be connected to a motor external to the device via a flexible torque cable.

According to one aspect, the therapeutic substance is front-loaded into a delivery device through the dispensing end of the device. Such an arrangement may help reduce waste or loss of the therapeutic substance (e.g., by avoiding transfer of the substance through multiple components).

In some embodiments, the delivery device may include an air vent arrangement to permit front-loading. In some embodiments, during loading of the delivery device, drawing the therapeutic substance into the needle lumen displaces air from the needle lumen. In some embodiments, a vent is provided to allow the displaced air to be vented out of the needle lumen. In some embodiments, this venting arrangement may help to avoid or lessen pressurization of the therapeutic substance and/or the needle lumen. In some embodiments, this venting arrangement may help to avoid air and the therapeutic substance from competing for volume space. In some embodiments, this venting arrangement may help to decrease introduction of air bubbles into the therapeutic substance.

In the illustrative embodiment shown in FIG. 3B, the needle 50 includes the vent 59 in the form of a through-hole opening that extends through a wall 57 of the needle 50. The vent 59 is opened or closed based on the position of the plunger 60. When the distal end 65 of the plunger 60 is distal to the vent 59, as shown in FIG. 3B, the vent 59 is closed. When the distal end 65 of the plunger 60 is proximal to the vent 59, the vent 59 is open.

Figure 10B:
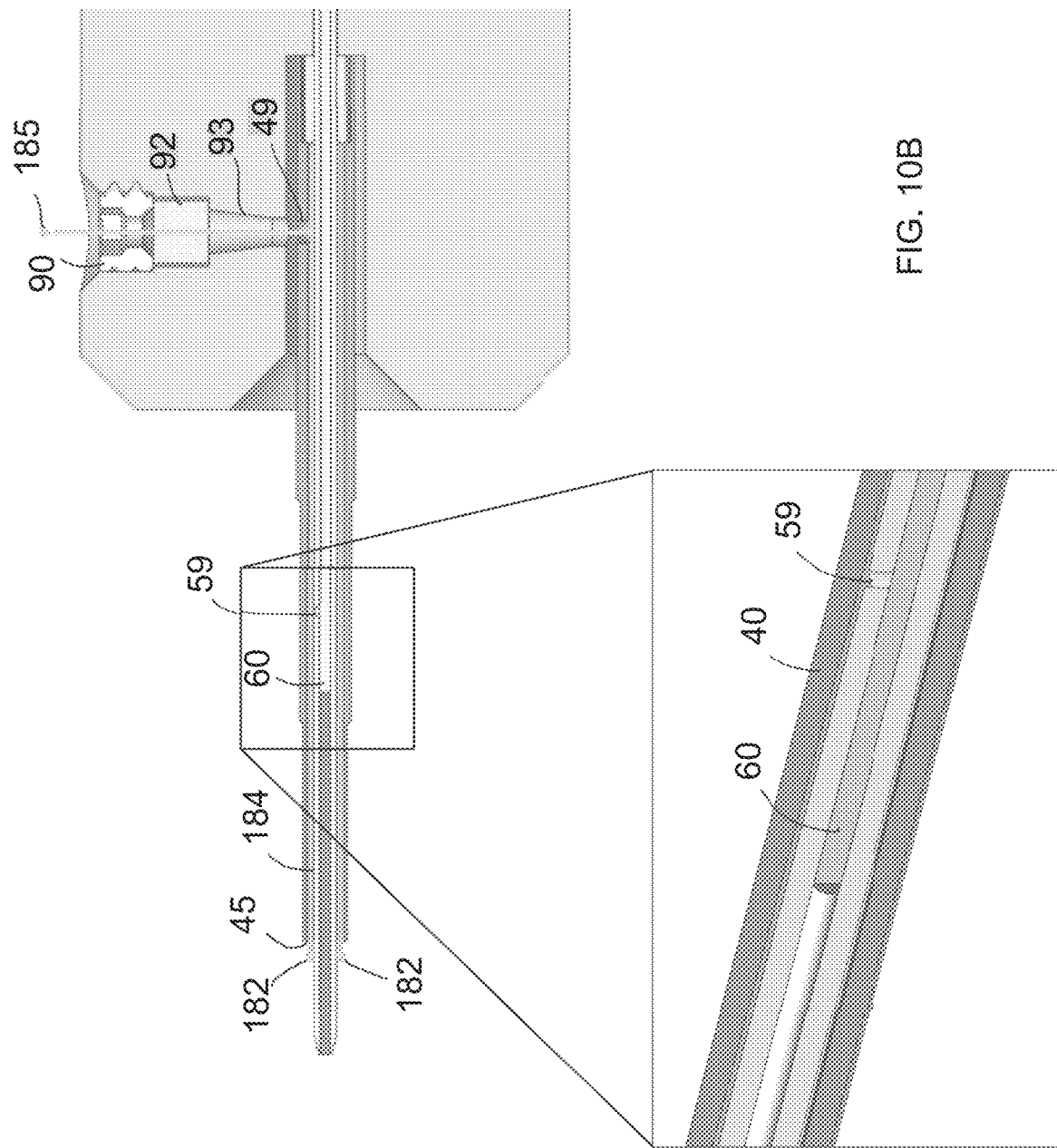
FIG. 10B is a cross-sectional view of the delivery device of FIG. 10A undergoing a flushing process, according to one embodiment.

A front-loading sequence according to some embodiments is depicted in FIGS. 10A-10C. With the vent 59 in an open state, as shown in FIG. 10A, a therapeutic substance 180 is moved into the needle lumen 51 through the needle opening 58 in a proximal loading direction 181. As the therapeutic substance 180 is moved into the needle lumen 51, air that previously occupied the needle lumen 51 is vented out through the open vent 59 and into the shaft lumen 41.

In some embodiments, the delivery device is passively loaded with therapeutic substance, e.g., the delivery device itself is not actuated during loading. An active loading device, such as a pump, may be used to move the therapeutic substance into the needle lumen. The pump may be a syringe pump or any other suitable pump. In some embodiments, the therapeutic substance is transferred from a holder into the needle lumen.

Next, as shown in FIG. 10B, the vent 59 is closed. In some embodiments, a user closes the vent 59 by actuating the device actuator 30 to advance the plunger 60 distally until the distal end 65 of the plunger is distal to the vent 59.

In some embodiments, a flushing step is performed to remove air from the outer lumen, in the space between the outer shaft and the needle. As shown in FIG. 10B, a delivery device includes a flushing port 90. A flushing fluid 184, such as a transplantation medium, may be injected through the flushing port 90 in flushing direction 185, and through a valve 92, channel 93 and an opening 49 in the outer shaft 40. The transplantation medium may travel through the space between the outer shaft 40 and the needle 50, as indicated with arrows 182. The user may observe flushing fluid exiting a distal end 45 of the outer shaft 40, indicating to the user that the device is primed and ready for delivery into tissue. FIG. 10C depicts a primed device that is ready for delivery, with the therapeutic substance 180 loaded into the needle lumen, the plunger 60 covering the vent 59, and air flushed out of the cannula portion 9.

The inventors have appreciated that after the therapeutic substance is expelled from the needle into the volume of space at the target site 215 created by the withdrawal of the needle, a suction effect is created as the cannula portion 9 is withdrawn from the tissue in which it is inserted. The suction effect can pull a portion of the therapeutic substance out of the target site 215 and thereby reduce a dose of the therapeutic substance delivered to the target site 215.

The delivery device can be configured to mitigate the suction effect experienced during the withdrawal of the cannula portion 9 from the tissue. For example, the valve 92 of the flushing port 90 can be configured to be set in an open position to expose the inside of the cannula portion 9 and in particular the space between the outer shaft 40 and the needle 50 to atmospheric pressure to drain the flushing fluid 184 into the tissue as the cannula portion 9 is withdrawn from the tissue. The valve 92 can be configured to receive, for example, a device such as an open needle to expose the space between the outer shaft 40 and the needle 50 to atmospheric pressure to drain the flushing fluid 184 into the tissue as the cannula portion 9 is withdrawn from the tissue. The draining of the flushing fluid 184 toward the target site 215 can counter the suction effect to thereby mitigate the reduction in the dose of the therapeutic substance delivered to the target site 215 as the cannula portion 9 is withdrawn from the tissue.

According to one aspect, the delivery device may include an indicator comprising only mechanical components. Such an arrangement may permit the delivery device to be more portable and/or easier to sterilize due to a lack of electrical components.

Figure 11:
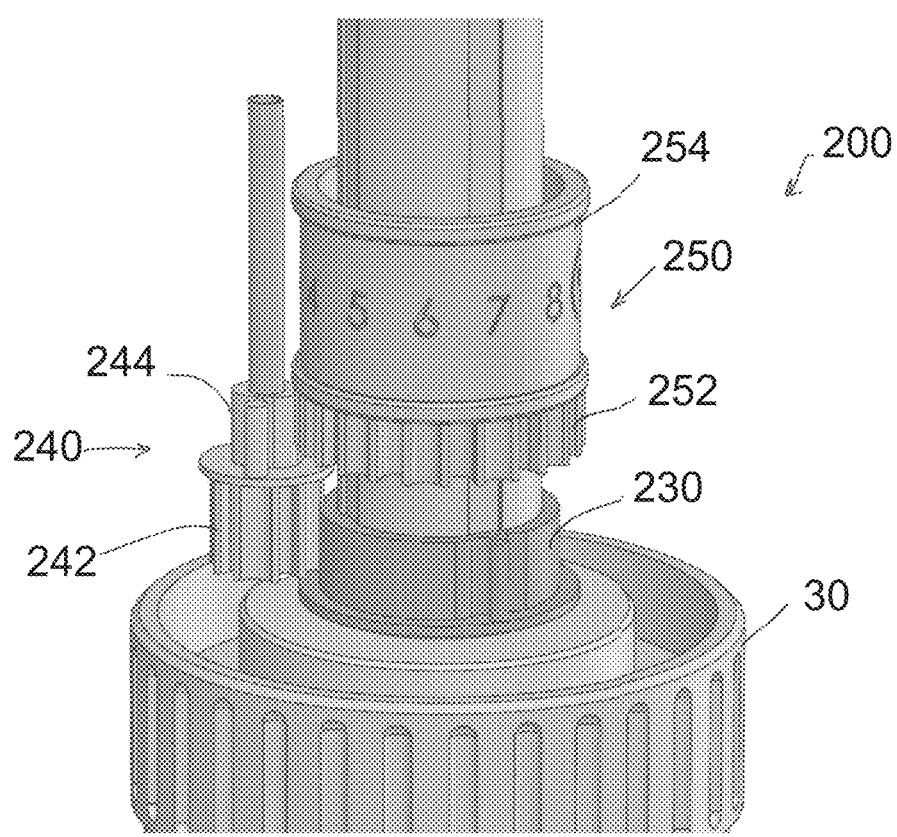
FIG. 11 is a perspective view of an indicator assembly, according to one embodiment.

In some embodiments, a gearing system may be used to transmit the actuation force imparted to the device actuator to movement of a component having indicia reflecting the volume that has been delivered and/or indicia reflecting the state of the device (e.g. ready to be loaded with a therapeutic substance). One illustrative embodiment of a mechanical indicator is shown in FIG. 11. The indicator arrangement of FIG. 11 uses a Geneva gear system 200. The Geneva gear system 200 includes a first drive wheel 230 that may turn in 1:1 ratio with the device actuator 30. The first drive wheel 230 interacts with and drives a driven wheel portion 242 of a gear assembly 240. The gear assembly 240 also includes a drive wheel portion 244 that interacts with and drives a driven wheel portion 252 of an indicator gear 250. The indicator gear 250 also includes an indicia portion 254. As shown in FIGS. 1 and 2, indicia of the indicia portion 254 is visible through an indicator window 255 of the delivery device. As the device actuator 30 is actuated, the indicia portion 254 turns, reflecting the volume that has been delivered.

While a Geneva gear system is used in the illustrative embodiment of FIG. 11 to link the device actuator 30 to the indicia portion 254, it should be appreciated that any other suitable gear system or force transmitting system could be used. In some embodiments, the delivery device uses a digital display to indicate delivery volume and/or communicate any other suitable information.

Figure 12:
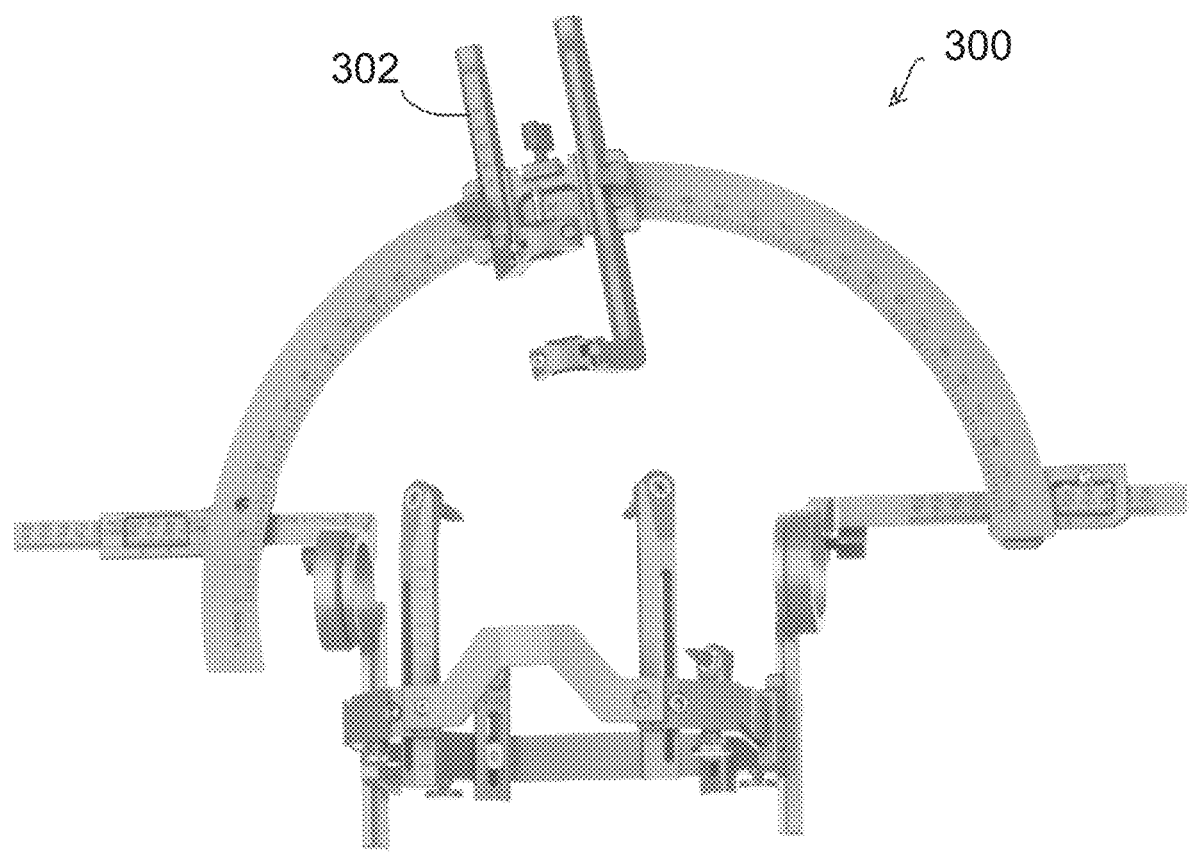
FIG. 12 is a stereotactic frame for use with the delivery device, according to one embodiment.

In some embodiments, any one of the delivery devices described herein may be used with a stereotactic frame, e.g., for neurosurgical applications. An illustrative example of a stereotactic frame is shown in FIG. 12. The stereotactic frame 300 includes an arm 302 for receiving a delivery device. In some embodiments, the delivery device may be sized to be physically compatible with a stereotactic frame. In the illustrative embodiment shown in FIG. 3A, the delivery device 1 includes a seating connector 80 that is sized to fit with an arm of a stereotactic frame. The seating connector of the delivery device may be held by the stereotactic frame. In some embodiments, the delivery device is compatible with stereotactic frames from LEKSELL. However, it should be appreciated that the delivery device may be compatible with other stereotactic frames, as this aspect is not so limited.

In some embodiments, the delivery device is compatible with frameless stereotactic systems. As an example, a subject's head (including the targeted tissue) may be fixed with a clamp such as a standard Mayfield clamp. Further, the delivery device can include a portion of a tracking system for tracking the position and angulation of the delivery device. The tracking system can include one or more of an optical-based tracking system and an electromagnetic tracking system. The optical-based tracking system can include one or more optical cameras configured to track one or more recognizable structures built into or provided to the delivery device or to track one or more unique optical wavelengths emitted from an emitter built into or provided to the delivery device. The optical-based tracking system can utilize techniques such as distance measurement using the principle of parallax, object recognition and other image processing techniques to calculate the position and the angulation of the delivery device relative to the subject's head. The electromagnetic tracking system can include one or more electromagnetic field emitters and one or more electromagnetic field detectors. One of the one or more electromagnetic field emitters and the one or more electromagnetic field detectors can be built into or provided to the delivery device while the other of the one or more electromagnetic field emitters and the one or more electromagnetic field detectors can be arranged in a vicinity of the delivery device. The electromagnetic tracking system can calculate the position and the angulation of the delivery device relative to the subject's head based on the known values of the electromagnetic field emitted by the one or more electromagnetic field emitters and the electromagnetic fields detected by the one or more electromagnetic field detectors. The position and the angulation of the delivery device calculated by the tracking system can be output as a visual guide for guiding the insertion of the delivery device. The position and the angulation of the delivery device calculated by the tracking system can also be output to a robotic system that controls one or more actuators to guide the insertion of the delivery device. The position and the angulation of the delivery device calculated by the tracking system can also be superimposed on images acquired through imaging systems such as computed tomography, magnetic resonance imaging and positron emission tomography to aid in the insertion of the delivery device. It should be appreciated that the delivery device may be compatible with other frameless stereotactic systems, as this aspect is not so limited.

In use, in some embodiments, the needle is deployed into tissue by advancing the entire delivery device distally. If the delivery device is attached to a stereotactic frame, the frame may assist in guiding distal movement of the delivery device. Then, to deliver the therapeutic substance, the operator may actuate the device actuator.

It should be appreciated that, in some embodiments, the needle can be actuated to move in a deployment direction relative to the outer shaft and/or relative to the housing of the delivery device. In some embodiments, a single device actuator may be used to move both the needle in the deployment direction and to eject a therapeutic substance. In other embodiments, a first actuator is used to move the needle in the deployment direction, and a second actuator is used to eject the therapeutic substance.

Figure 13:
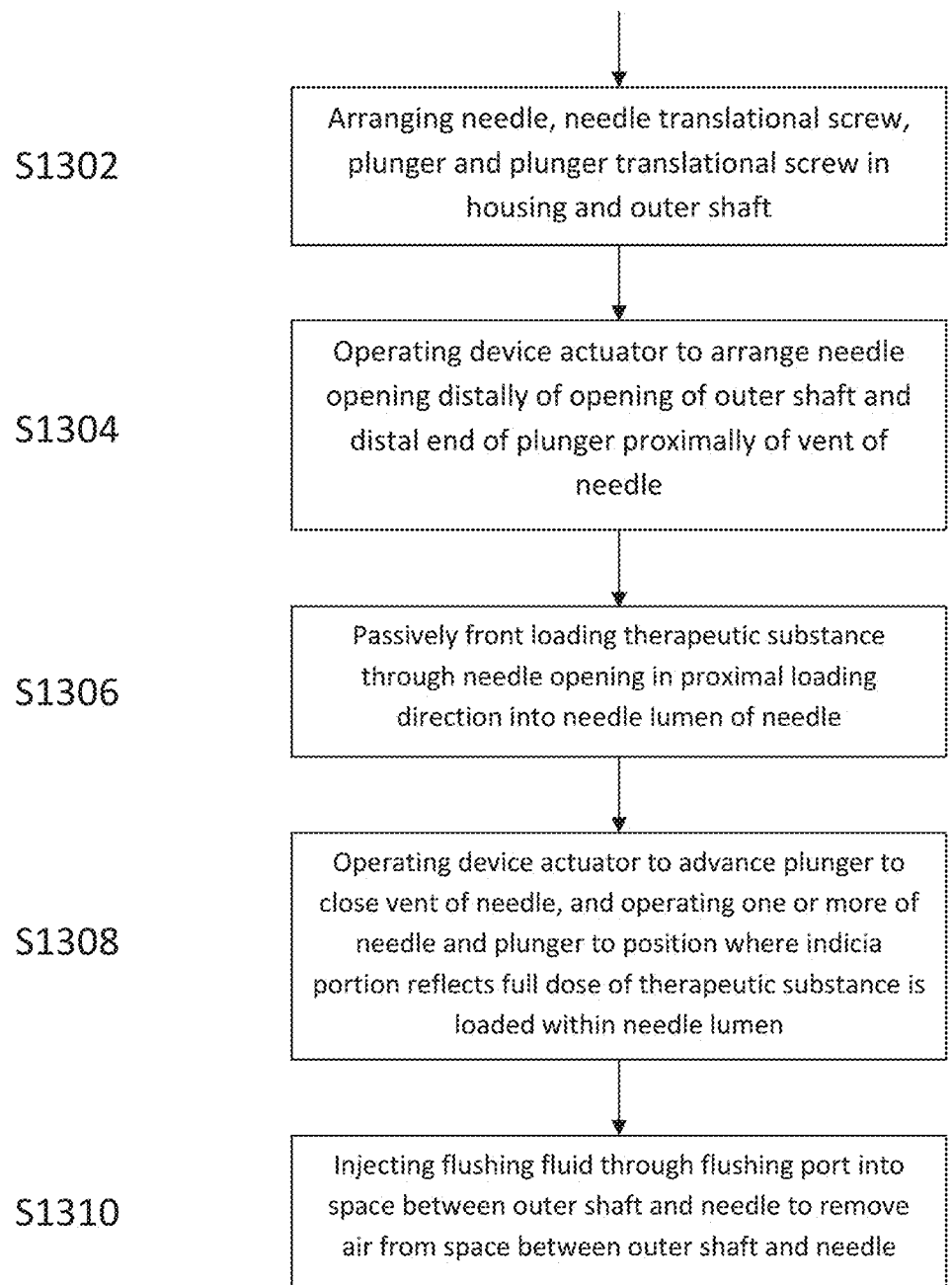
FIG. 13 is a flowchart of a method for preparing and priming a delivery device for use, according to one embodiment.

Next, a method for preparing and priming the delivery device for use will be described with reference to FIG. 13. The method can include a step S1302. The step S1302 can include arranging one or more of the needle 50, the needle translational screw 52 attached to the needle 50, the plunger 60 and the plunger translational screw 62 attached to the plunger 60 in the housing 10 and the outer shaft 40 of the delivery device. For example, the needle translational screw 52 can be arranged to engage the first threaded passage 56 and the plunger translational screw 62 can be arranged to engage the second threaded passage 66 within the housing 10. Further, the plunger 60 can be arranged within the needle lumen 51 of the needle 50, and needle 50 having the plunger 60 arranged therein can be arranged within the shaft lumen 41 of the outer shaft 40. The step S1302 can allow for the needle 50 and the plunger 60 to be replaced with needles and plungers of the same type. Further, the step S1302 can allow for needles 50 of different types (e.g., needles 50 having needle lumens 51 with different volumes) and corresponding plungers 60 to be selected and arranged within the housing 10 of the delivery device.

After the step S1302, a step S1304 can be performed. The step S1304 can include operating the device actuator 30 to cause relative movement of the needle 50 and the plunger 60 to arrange the needle opening 58 distally of the opening 45 of the outer shaft 40 in the longitudinal axis 4 and the distal end 65 of the plunger 60 proximally of the vent 59 of the needle 50 as illustrated in FIG. 10A.

After the step S1304, a step S1306 can be performed. The step S1306 can include passively front loading the therapeutic substance 180 into the needle lumen 51 of the needle 50 as illustrated in FIG. 10A. For example, an active loading device, such as a pump, may be used to move the therapeutic substance 180 through the needle opening 58 in the proximal loading direction 181 into the needle lumen 51. Since the distal end 65 of the plunger 60 is moved proximally of the vent 59 of the needle 50 in step S1304, as the therapeutic substance 180 is moved into the needle lumen 51, air that previously occupied the needle lumen 51 is vented out through the open vent 59 into the shaft lumen 41.

After the step S1306, a step S1308 can be performed. The step S1308 can include operating the device actuator 30 to advance the distal end of the plunger 60 to a position distal of the vent 59 as illustrated in FIG. 10B to close vent 59 of the needle 50. The step S1308 can also include operating the device actuator 30 to move one or more of the needle 50 and the plunger 60 and simultaneously drive an indicator arrangement to a position where an indicia reflects that a full dose (of a target volume) of the therapeutic substance 180 is loaded within the needle lumen 51.

After the step S1308, a step S1310 can be performed. The step S1310 can include injecting the flushing fluid 184 through the flushing port 90 of the delivery device and the opening 49 of the outer shaft 40 in the flushing direction 185 as illustrated in FIG. 10B into the space between the outer shaft 40 and the needle 50 to remove air from the space between the outer shaft 40 and the needle 50. The injection of the flushing fluid 184 can be performed until the flushing fluid 184 is observed to exit the distal end 45 of the outer shaft 40. At this point the delivery device can be considered to be in a primed state as illustrated in FIG. 10C.

It is noted that the method for preparing and priming the delivery device can include a portion of the above-described steps while omitting one or more of the above-described steps. In a situation where the delivery device is intended for a single use, the step S1302 of arranging the needle 50, the needle translational screw 52, the plunger 60 and the plunger translational screw 62 in the housing 10 can be omitted. Alternatively, in a situation where the housing 10 is configured to house needles and plungers of different types, the step S1302 can be included in the method.

Figure 14:
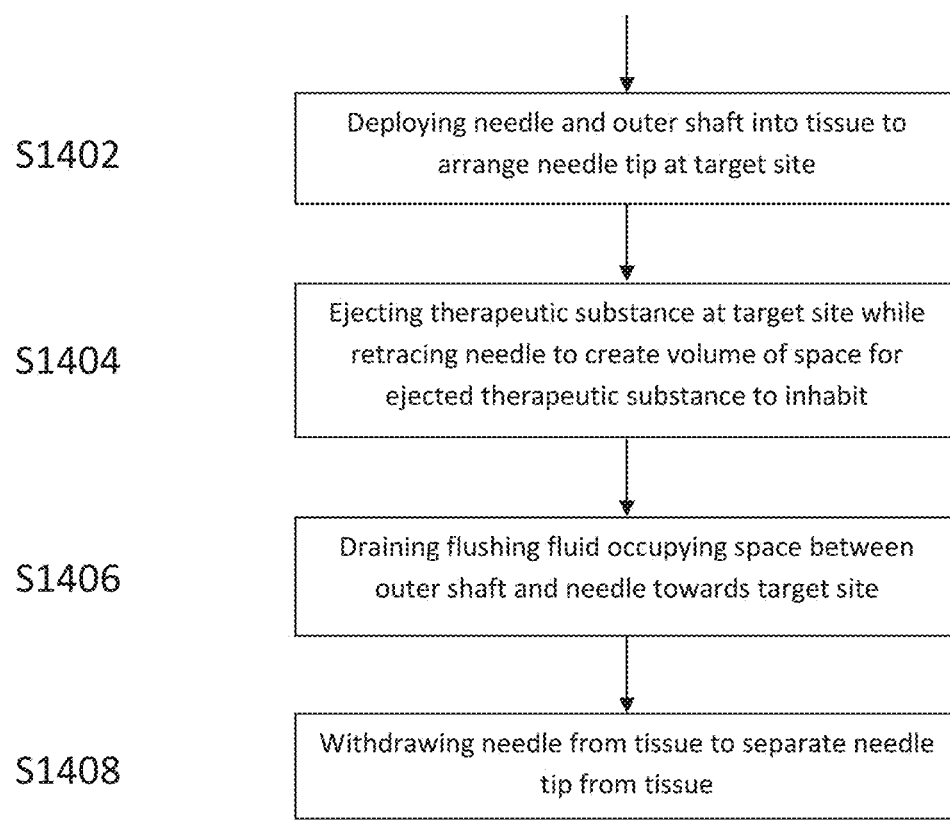
FIG. 14 is a flowchart of a method for using a delivery device, according to one embodiment.

Next, a method for using the delivery device will be described with reference to FIG. 14. The method can include a step S1402. The step 1402 can include deploying the needle 50 and the outer shaft 40 into the tissue. Deploying the needle 50 and the outer shaft 40 into the tissue can include advancing the entire delivery device distally to arrange the needle tip 55 at the target site 215. Advancing the entire delivery device can be performed manually. Alternatively, advancing the entire delivery device can include guiding the delivery device by a stereotactic frame or a frameless stereotactic system to guide the delivery device to position the needle tip 55 at the target site 215.

After the step S1402, a step 1404 can be performed. The step S1404 can include operating the device actuator 30 to eject the therapeutic substance 180 at the target site 215. Ejecting the therapeutic substance 180 can include moving the plunger 60 relative to the needle 50 by moving one or both of the plunger 60 and the needle 50 to eject the therapeutic substance 180. Specifically, ejecting the therapeutic substance 180 can include retracting the needle 50 to create a volume of space for the therapeutic substance 180 ejected from the delivery device to inhabit to thereby reduce the backflow of the therapeutic substance 180 out of the target site 215.

After the step S1404, a step S1406 can be performed. The step S1406 can include draining the flushing fluid 184 occupying the space between the outer shaft 40 and the needle 50 toward the target site 215. Draining the flushing fluid 184 can include setting the valve 92 of the flushing port 90 to an open position to expose the space between the outer shaft 40 and the needle 50 to atmospheric pressure to drain the flushing fluid 184 into the tissue. For example, a device such as an open needle can be inserted into the valve 92 to set the valve 92 to the open position.

After the step S1406, a step S1408 can be performed. The step 1408 can also be performed together with step S1406. The step S1408 can include withdrawing the needle 50 and the outer shaft 40 from the tissue. Withdrawing the needle 50 and the outer shaft 40 from the tissue can include retracting the entire delivery device proximally to separate the needle tip 55 and the outer shaft 40 from the tissue. Retracting the entire delivery device can be performed manually. Alternatively, retracting the entire delivery device can include guiding the delivery device by the stereotactic frame or the frameless stereotactic system to separate the needle tip 55 and the outer shaft 40 from the tissue.

It is noted that the method for using the delivery device can include a portion of the above-described steps while omitting one or more of the above-described steps. For example, the step S1406 of draining the flushing fluid 184 can be omitted if the risk of the suction effect caused by withdrawing the needle 50 from the tissue is considered to be small.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A delivery device, comprising:
a device actuator;
a needle having a needle lumen; and
a plunger that is configured to move through the needle lumen,
wherein actuation of the device actuator causes the needle to move in a retraction direction and causes the plunger to move through the needle lumen in a deployment direction, the retraction direction being opposite to the deployment direction, and
wherein movement of the needle occurs simultaneously with movement of the plunger.

2. The delivery device of claim 1, further comprising an outer shaft having a shaft lumen, the needle being configured to move through the shaft lumen.

3. The delivery device of claim 2,
wherein actuation of the device actuator causes the needle to move a first distance relative to the outer shaft and causes the plunger to move a second distance relative to the outer shaft, the first distance being different from the second distance.

4. The delivery device of claim 3, wherein the first distance is smaller than the second distance.

5. The delivery device of claim 3, wherein a ratio of the second distance to the first distance is about 2:1 to about 20:1.

6. The delivery device of claim 5, wherein the ratio is 10:1.

7. The delivery device of claim 1, further comprising:
a first threaded passage;
a second threaded passage;
a first translation screw attached to the needle and positioned within the first threaded passage; and
a second translation screw attached to the plunger and positioned within the second threaded passage,
wherein actuation of the device actuator causes rotation of the first threaded passage and rotation of the second threaded passage, which causes the first translation screw to translate through the first threaded passage and causes the second translation screw to translate through the second threaded passage.

8. The delivery device of claim 7,
wherein the rotation of the first threaded passage occurs in a first rotational direction, and the rotation of the second threaded passage occurs in a second rotational direction opposite to the first rotational direction.

9. The delivery device of claim 8,
wherein the first threaded passage has a first thread having a first thread count, and the second threaded passage has a second thread having a second thread count, the first and second thread counts being different.

10. The delivery device of claim 9,
wherein the first thread count is larger than the second thread count.

11. The delivery device of claim 8,
wherein the first threaded passage has a first thread having a first thread orientation, and the second threaded passage has a second thread having a second thread orientation, the first and second thread orientations being opposite to one another.

12. The delivery device of claim 11,
wherein the first thread orientation is a right-handed thread, and the second thread orientation is a left-handed thread.

13. The delivery device of claim 8, further comprising a gear system that couples the device actuator to the first threaded passage.

14. The delivery device of claim 13,
wherein the gear system comprises a planetary gear system comprising a sun gear and a plurality of planetary gears, the planetary gears being rotatably mounted on a carrier, and
wherein the sun gear is coupled to the device actuator and to the second threaded passage, and wherein the carrier is coupled to the first threaded passage.

15. The delivery device of claim 1, further comprising a gear system that connects the device actuator to the plunger and the needle.

16. The delivery device of claim 15,
wherein the gear system comprises a planetary gear system having a sun gear and a plurality of planetary gears, the planetary gears being rotatably mounted to a carrier, and
wherein the sun gear is attached to the device actuator and coupled to the plunger, and wherein the carrier is coupled to the needle.

17. The delivery device of claim 1,
wherein the needle lumen has a constant diameter throughout the length of the needle.

18. The delivery device of claim 1,
wherein, in response to device actuation, a volume of space through which the plunger moves is within 1 to 20 percent of a volume of space through which the needle moves.

19. A delivery device, comprising:
a device actuator;
an outer shaft having a shaft lumen;
a needle having a needle lumen, the needle being configured to move through the shaft lumen; and
a plunger that is configured to move through the needle lumen,
wherein actuation of the device actuator causes the needle to move a first distance relative to the outer shaft and causes the plunger to move a second distance relative to the outer shaft, the first distance being different from the second distance, and
wherein the first distance is smaller than the second distance.

20. The delivery device of claim 19,
wherein a ratio of the second distance to the first distance is about 2:1 to about 20:1.

21. The delivery device of claim 20,
wherein the ratio is about 7:1 to about 10:1.

22. The delivery device of claim 19,
wherein the first distance is about 0.1 inch to about 1 inch.

23. The delivery device of claim 22,
wherein the first distance is about 0.3 inches to about 0.7 inches.

24. The delivery device of claim 19,
wherein the second distance is about 3 inches to about 7 inches.

25. The delivery device of claim 24,
wherein the second distance is about 4 inches to 5 inches.

26. The delivery device of claim 19,
wherein actuation of the device actuator causes the needle to move through the shaft lumen in a retraction direction and causes the plunger to move through the needle lumen in a deployment direction, the retraction direction being opposite to the deployment direction.

27. The delivery device of claim 19, further comprising:
a first threaded passage;
a second threaded passage;
a first translation screw attached to the needle and positioned within the first threaded passage; and
a second translation screw attached to the plunger and positioned within the second threaded passage,
wherein actuation of the device actuator causes rotation of the first threaded passage and rotation of the second threaded passage, which causes the first translation screw to translate through the first threaded passage and causes the second translation screw to translate through the second threaded passage.

28. The delivery device of claim 27,
wherein the rotation of the first threaded passage occurs in a first rotational direction, and the rotation of the second threaded passage occurs in a second rotational direction opposite to the first rotational direction.

29. The delivery device of claim 27,
wherein the first threaded passage has a first thread having a first thread count, and the second threaded passage has a second thread having a second thread count, the first and second thread counts being different.

30. The delivery device of claim 29,
wherein the first thread count is smaller than the second thread count.

31. The delivery device of claim 27,
wherein the first threaded passage has a first thread having a first thread orientation, and the second threaded passage has a second thread having a second thread orientation, the first and second thread orientations being opposite to one another.

32. The delivery device of claim 31,
wherein the first thread orientation is a left-handed thread, and the second thread orientation is a right-handed thread.

33. The delivery device of claim 27, further comprising a gear system that connects the device actuator to the first threaded passage and the second threaded passage.

34. The delivery device of claim 33,
wherein the gear system comprises a planetary gear system having a sun gear and a plurality of planetary gears, the planetary gears being rotatably mounted to a carrier, and
wherein the sun gear is attached to the device actuator and to the second threaded passage, and wherein the carrier is attached to the first threaded passage.

35. The delivery device of claim 27, further comprising a gear system that connects the device actuator to the plunger and the needle.

36. The delivery device of claim 35,
wherein the gear system comprises a planetary gear system having a sun gear and a plurality of planetary gears, the planetary gears being rotatably mounted to a carrier, and
wherein the sun gear is attached to the device actuator and coupled to the plunger, and wherein the carrier is coupled to the needle.

37. A delivery device, comprising:
a device housing;
a device actuator that is rotatably mounted relative to the device housing;
a needle having a needle lumen; and
a plunger that is configured to move through the needle lumen,
wherein an outer diameter of a distal end portion of the plunger is set to provide a seal against the needle lumen, and
wherein rotation of the device actuator causes the distal end portion of the plunger to move through the needle lumen.

38. The delivery device of claim 37,
wherein the device actuator has a rotation axis that is parallel with an extension direction of the plunger.

39. The delivery device of claim 37,
wherein a plurality of complete rotations of the device actuator is required to achieve a maximum delivery volume.

40. The delivery device of claim 39,
wherein the plurality of complete rotations comprises 5 to 40 rotations.

41. The delivery device of claim 40,
wherein the plurality of complete rotations comprises 15 to 30 rotations.

42. The delivery device of claim 39,
wherein the maximum delivery volume comprises 5 to 15 microliters.

43. The delivery device of claim 42,
wherein the maximum delivery volume comprises 9 microliters.

44. The delivery device of claim 37, further comprising a gear system that couples the device actuator to the plunger and the needle.

45. The delivery device of claim 44,
wherein the gear system comprises a planetary gear system having a sun gear and a plurality of planetary gears, the planetary gears being rotatably mounted to a carrier, and
wherein the sun gear is attached to the device actuator and coupled to the plunger, and wherein the carrier is coupled to the needle.

46. The delivery device of claim 45,
wherein the sun gear and the device actuator are integrally formed as a single part.

47. A delivery device, comprising:
a device housing;
a needle having a delivery end, a shaft, and a needle lumen extending through the shaft; and
a plunger that is configured to move through the needle lumen,
wherein the needle further includes a vent in the shaft, the vent being spaced from the delivery end.

48. The delivery device of claim 47,
wherein the plunger has a first position in which fluid communication is open through the vent, and the plunger has a second position in which fluid communication is closed through the vent.

49. The delivery device of claim 47, further comprising a device actuator, wherein actuation of the device actuator moves the plunger in a deployment direction and closes fluid communication through the vent.

50. The delivery device of claim 47,
wherein the vent is a through-hole that extends through a wall of the shaft.

51. The delivery device of claim 47, further comprising:
a flushing port;
an outer shaft surrounding the needle, the outer shaft having an opening; and
a valve that controls fluid communication between the flushing port and the opening of the outer shaft.

52. The delivery device of claim 47, further comprising a therapeutic substance loaded into the delivery device, wherein the therapeutic substance is entirely contained within the needle lumen.

53. The delivery device of claim 52,
wherein the needle lumen has a constant diameter throughout its length.

54. A delivery device, comprising:
a device actuator;
an outer shaft having a shaft lumen;
a needle having a needle lumen, the needle lumen having a diameter of between 0.1 mm to 0.7 mm, inclusive, and the needle being configured to move through the shaft lumen; and
a plunger that is configured to move through the needle lumen, the plunger having a travel distance relative to the outer shaft of at least 100 mm,
wherein actuation of the device actuator causes the needle to move a first distance relative to the outer shaft and causes the plunger to move a second distance relative to the outer shaft, the first distance being different from the second distance, and
wherein the first distance is smaller than the second distance.

55. The delivery device of claim 54,
wherein the plunger has a seal portion and a body portion, the seal portion having a larger diameter than a diameter of the body portion.

56. The delivery device of claim 54,
wherein the delivery device is loaded with a therapeutic substance comprising a plurality of cells, wherein the cells have an average diameter of 10 to 15 microns.

57. The delivery device of claim 56,
wherein the cells comprise neural cells.

58. The delivery device of claim 57,
wherein the neural cells comprise dopaminergic neural cells.

59. A delivery device, comprising:
a device actuator;
a needle having a needle lumen;
a plunger that is configured to move through the needle lumen; and
an indicator having indicia indicating dosage delivered, the indicator being mechanically coupled to the device actuator such that actuation of the device actuator causes the indicia of the indicator to physically move without input of electricity.

60. The delivery device of claim 59, further comprising a gear system mechanically coupling the indicator to the device actuator.

61. The delivery device of claim 60,
wherein the gear system comprises a Geneva gear system.

62. A delivery device, comprising:
a device housing;
a needle having a needle lumen, the needle lumen having a constant diameter throughout its length;
a plunger that is configured to move through the needle lumen; and
a therapeutic substance that is entirely contained within the needle lumen.

* * * * *